US006821506B2

(12) United States Patent
Lanza et al.

(10) Patent No.: US 6,821,506 B2
(45) Date of Patent: Nov. 23, 2004

(54) SITE SPECIFIC BINDING SYSTEM, IMAGING COMPOSITIONS AND METHODS

(75) Inventors: Gregory M. Lanza, St. Louis, MO (US); Samuel A. Wickline, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 309 days.

(21) Appl. No.: 10/036,317

(22) Filed: Dec. 28, 2001

(65) Prior Publication Data

US 2002/0168320 A1 Nov. 14, 2002

Related U.S. Application Data

(62) Division of application No. 09/404,963, filed on Sep. 24, 1999, now Pat. No. 6,548,046, which is a continuation-in-part of application No. 09/189,118, filed on Nov. 9, 1998, now abandoned, which is a continuation of application No. 08/854,308, filed on May 12, 1997, now abandoned, which is a division of application No. 08/488,743, filed on Jun. 8, 1995, now Pat. No. 5,690,907.

(51) Int. Cl.$^7$ .............................................. A61B 5/055
(52) U.S. Cl. ...................................... 424/9.3; 424/9.34
(58) Field of Search ................................ 424/9.3, 9.32, 424/9.321, 9.37, 9.34; 600/410, 420

(56) References Cited

U.S. PATENT DOCUMENTS

| 4,863,713 A | 9/1989 | Goodwin et al. .......... 424/1.11 |
| 5,077,036 A | 12/1991 | Long, Jr. ..................... 424/5 |
| 5,114,703 A | 5/1992 | Wolf et al. ................... 424/5 |
| 5,171,737 A | 12/1992 | Weiner et al. ................ 514/3 |
| 5,242,681 A | 9/1993 | Elgavish et al. ............. 424/4 |
| 5,401,634 A | 3/1995 | Milbrath ..................... 435/6 |
| 5,512,294 A | 4/1996 | Li et al. ..................... 424/450 |
| 5,527,528 A | 6/1996 | Allen et al. ............... 424/178.1 |
| 5,536,489 A | 7/1996 | Lohrmann et al. ......... 424/9.52 |
| 5,542,935 A | 8/1996 | Unger et al. ............... 604/190 |
| 5,571,498 A | 11/1996 | Cacheris et al. ......... 424/9.365 |
| 5,585,112 A | 12/1996 | Unger et al. .............. 424/450 |
| 5,616,690 A | 4/1997 | Axworthy et al. .......... 530/363 |
| 5,922,304 A * | 7/1999 | Unger ....................... 424/9.3 |

FOREIGN PATENT DOCUMENTS

| DE | 42 32 755 | 3/1994 |
| EP | 0 251 494 | 1/1988 |
| EP | 0 727 225 | 8/1996 |
| EP | 0 274 431 | 7/1998 |
| WO | WO 95/03829 | 2/1995 |
| WO | WO 96/40285 | 12/1996 |

OTHER PUBLICATIONS

Hnatowich et al., Journal of Nuclear Medicine (1987) 28(8):1294–1302.
Hudson et al., Archives of Disease in Childhood (1990) 65(7);672–675.
Klibanov et al., Vestn Akad Med Navk SSSR (USSR) (1990) 8:50–54.
Lanza et al., "Specific Acoustic Enhancement of Vascular Thrombi in Vivo with a Naovel Site Targeted Ultrasonic Contrast Agent," Circulation (1995) 92(8)(Suppl):1260.
Lanza et al., "Initial Description and Validation of a Novel Site Targeted Ultrasonic Contrast Agents," Circulation (1995) 92(8)(Suppl):1260.
Lanza et al., Circulation (1996) 94(12):3334–3340.
Lanza et al., Ultrasound in Medicine and Biology (1997) 23(6):863–870.
Longman et al., Cancer Chemother. Pharmacol. (1995) 36(2):91–101.
Muzykantov et al., Journal of Nuclear Medicine (1994) 35(8): 1358–1365.
Urdal et al., Journal of Biological Chemistry (1980) 255(21):10509–10516.
Wallace et al., Circulation (1995) 92(8)(Suppl):1585.
Hudson et al., Archives of Disease in Childhood (1990) 65(7):672–675.
Lanza et al., "Specific Acoustic Enhancement of Vascular Thrombi in Vivo with a Naovel Site Targeted Ultrasonic Contrast Agent," Circulation (1995) 92(8)(suppl):1260.
Lanza et al., "Initial Description and Validation of a Novel Site Targeted Ultrasonic Contrast Agents," Circulation (1995) 92(8)(Suppl):1260.
Lanza et al., Circulation (1996) 94(12):334–3340.
Muzykantov et al., Journal of Nuclear Medicine (1994) 35(8):.

* cited by examiner

Primary Examiner—Michael G. Hartley
(74) Attorney, Agent, or Firm—Morrison & Foerster LLP

(57) ABSTRACT

A method for ligand-based binding of lipid encapsulated particles to molecular epitopes on a surface in vivo or in vitro comprises sequentially administering (a) a site specific ligand activated with a biotin activating agent; (b) an avidin activating agent; and (c) lipid encapsulated particles activated with a biotin activating agent, whereby the ligand is conjugated to the particles through an avidin-biotin interaction and the resulting conjugate is bound to the molecular epitopes on such surface. The conjugate is effective for imaging by x-ray, ultrasound, magnetic resonance or positron emission tomography. Compositions for use in ultrasonic imaging of natural or synthetic surfaces and for enhancing the acoustic reflectivity thereof are also disclosed.

12 Claims, 21 Drawing Sheets

Figure 18:
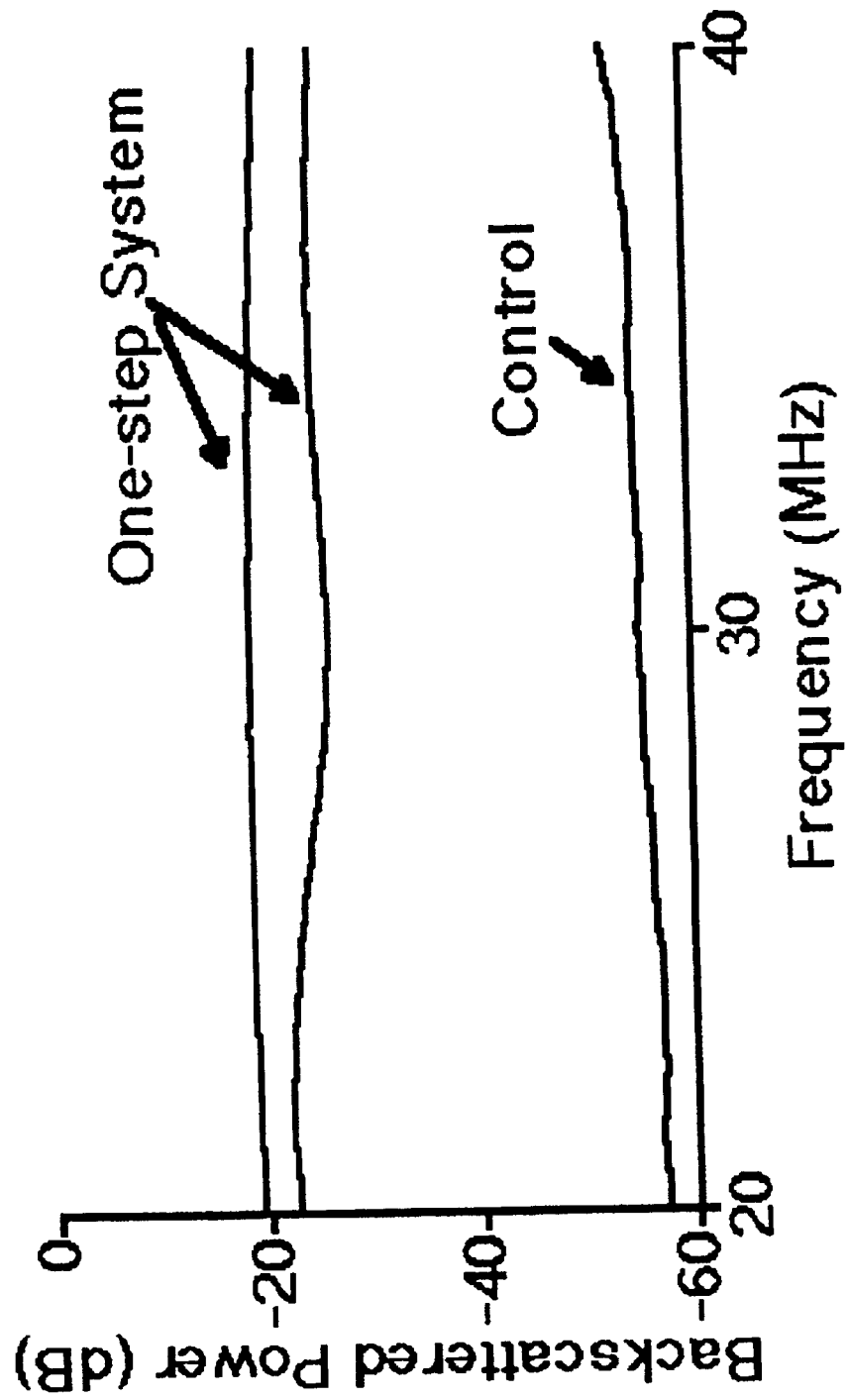

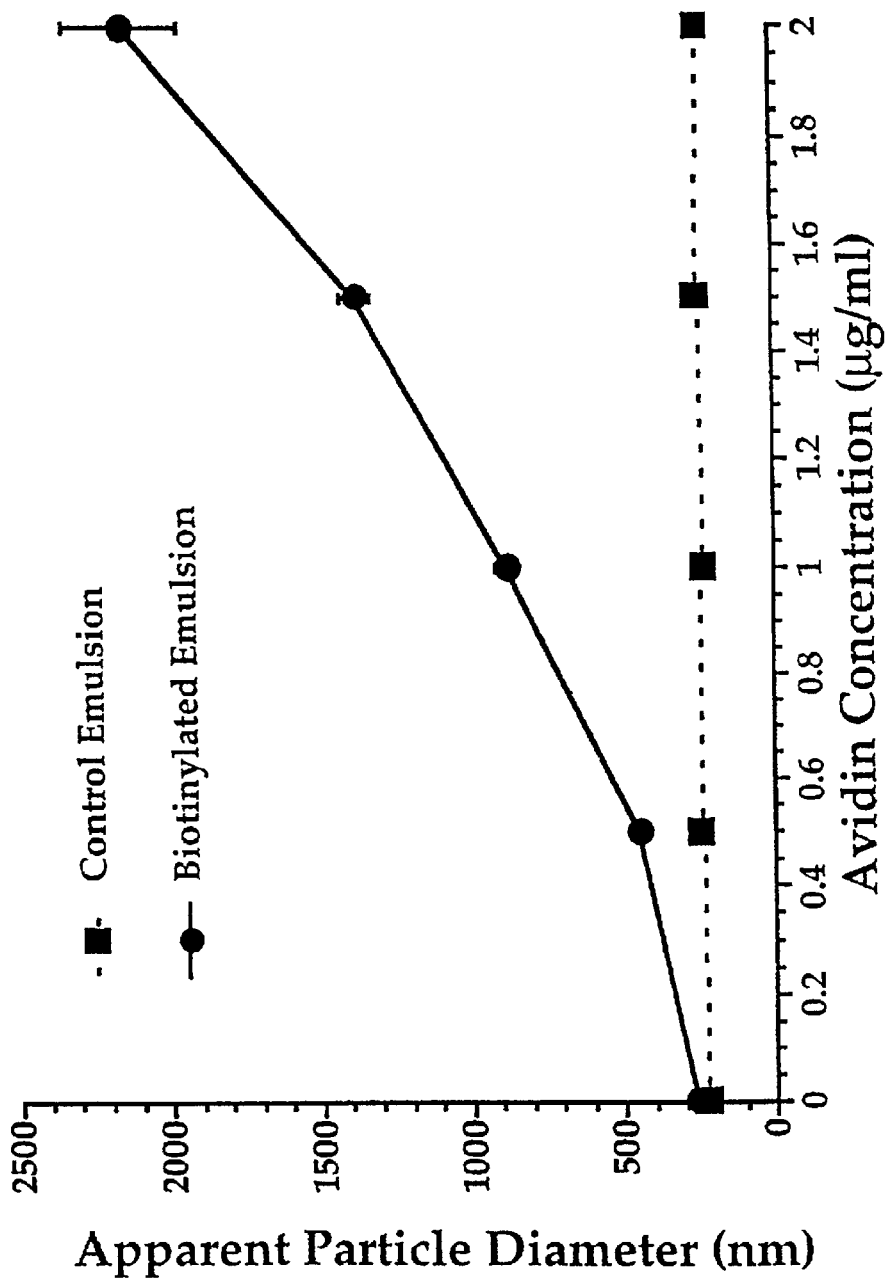
FIG. 1 Aggregate Particle Size Response of Control and Biotinylated Perfluorocarbon Emulsions to Titrated Levels of Avidin

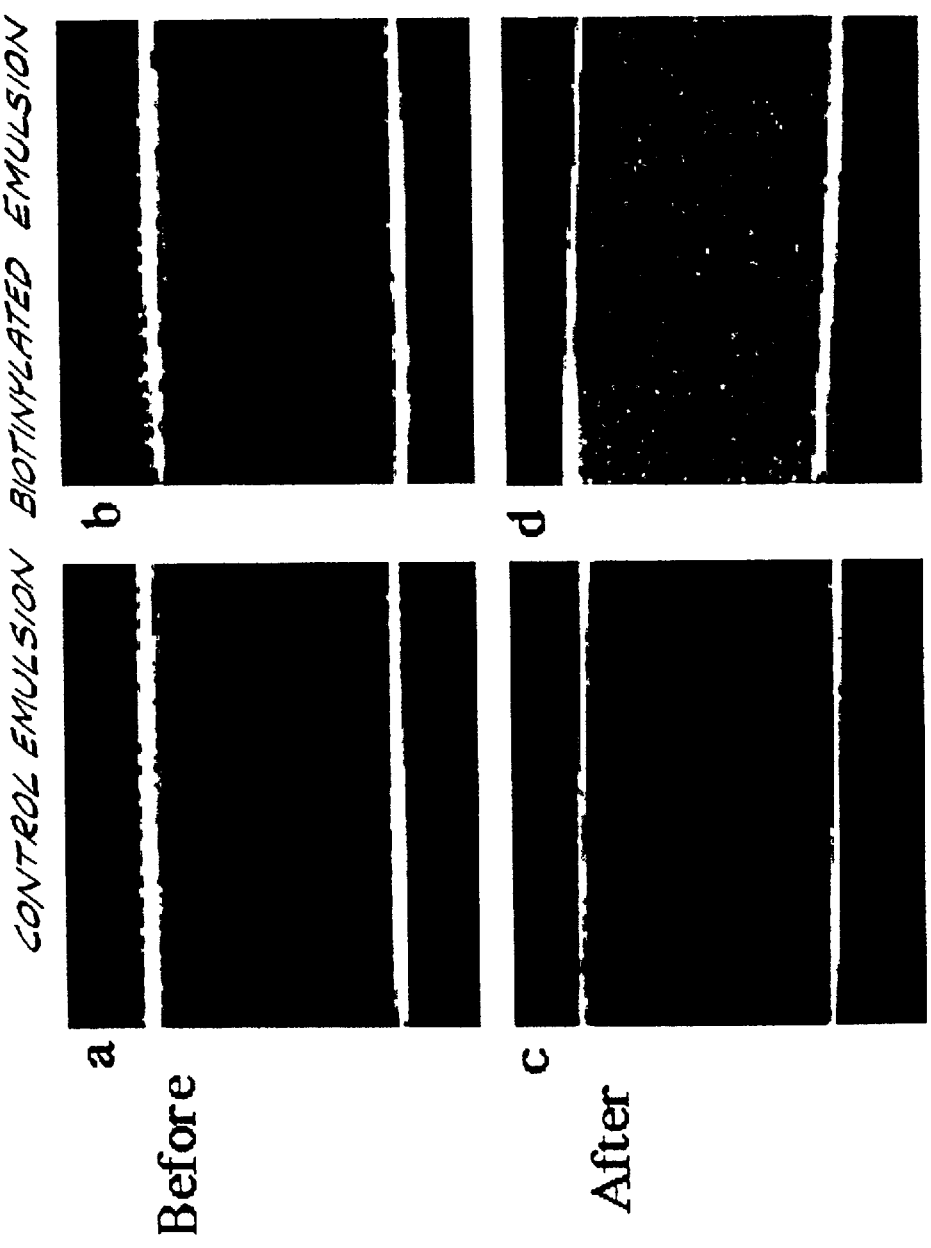
FIG.2 ULTRASONIC IMAGES OF CONTROL AND BIOTINYLATED PERFLUOROCARBON EMULSION BEFORE AND AFTER THE ADDITION OF AVIDIN

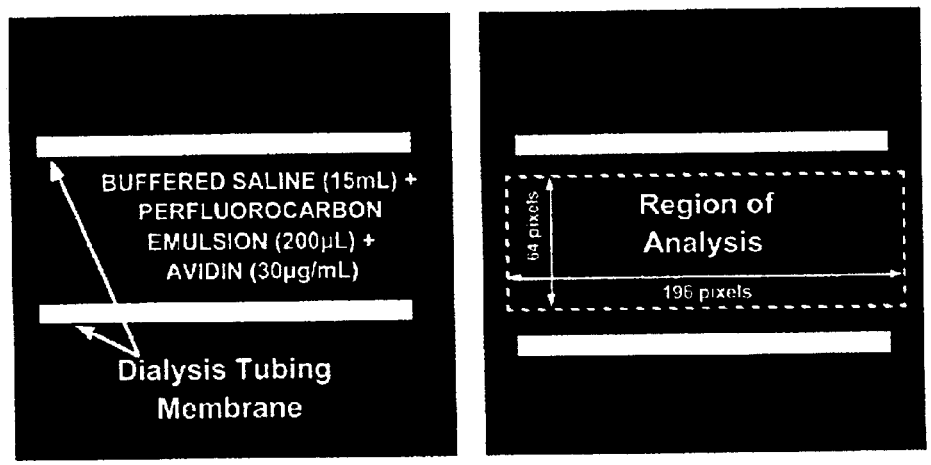
Figure 3. Graphic Illustration of Dialysis Tubing Images and Region of Interest Placement for Gray Scale Analysis

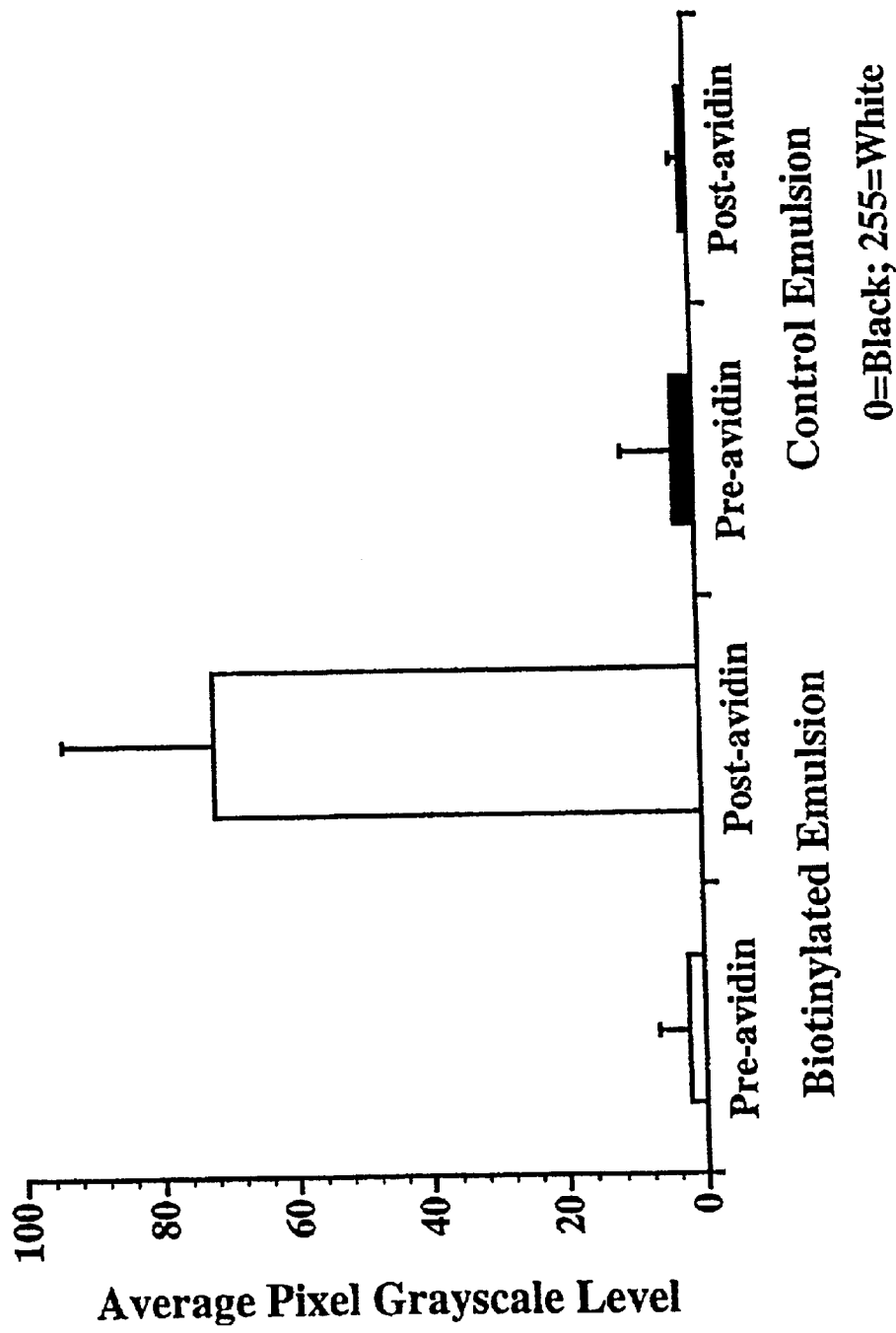
FIG. 4 Changes in Average Pixel Gray Scale Associated with the Addition of Avidin to Control or Biotinylated Perfluorocarbon Emulsion

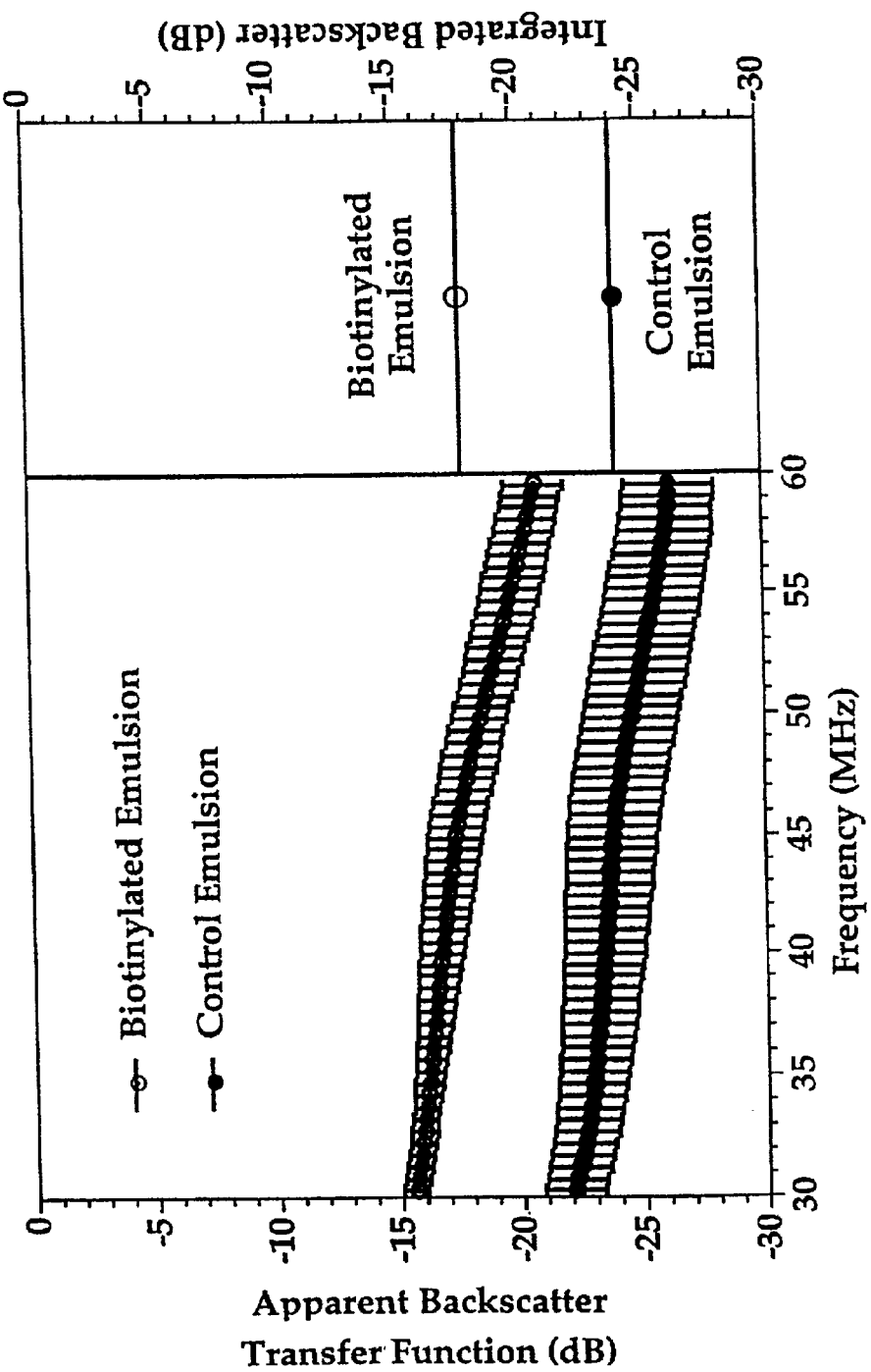
FIG. 5 The Effect of Control and Biotinylated Perfluorocarbon Emulsion on Apparent Backscatter Transfer Function and Integrated Backscatter of Avidinized Nitrocell

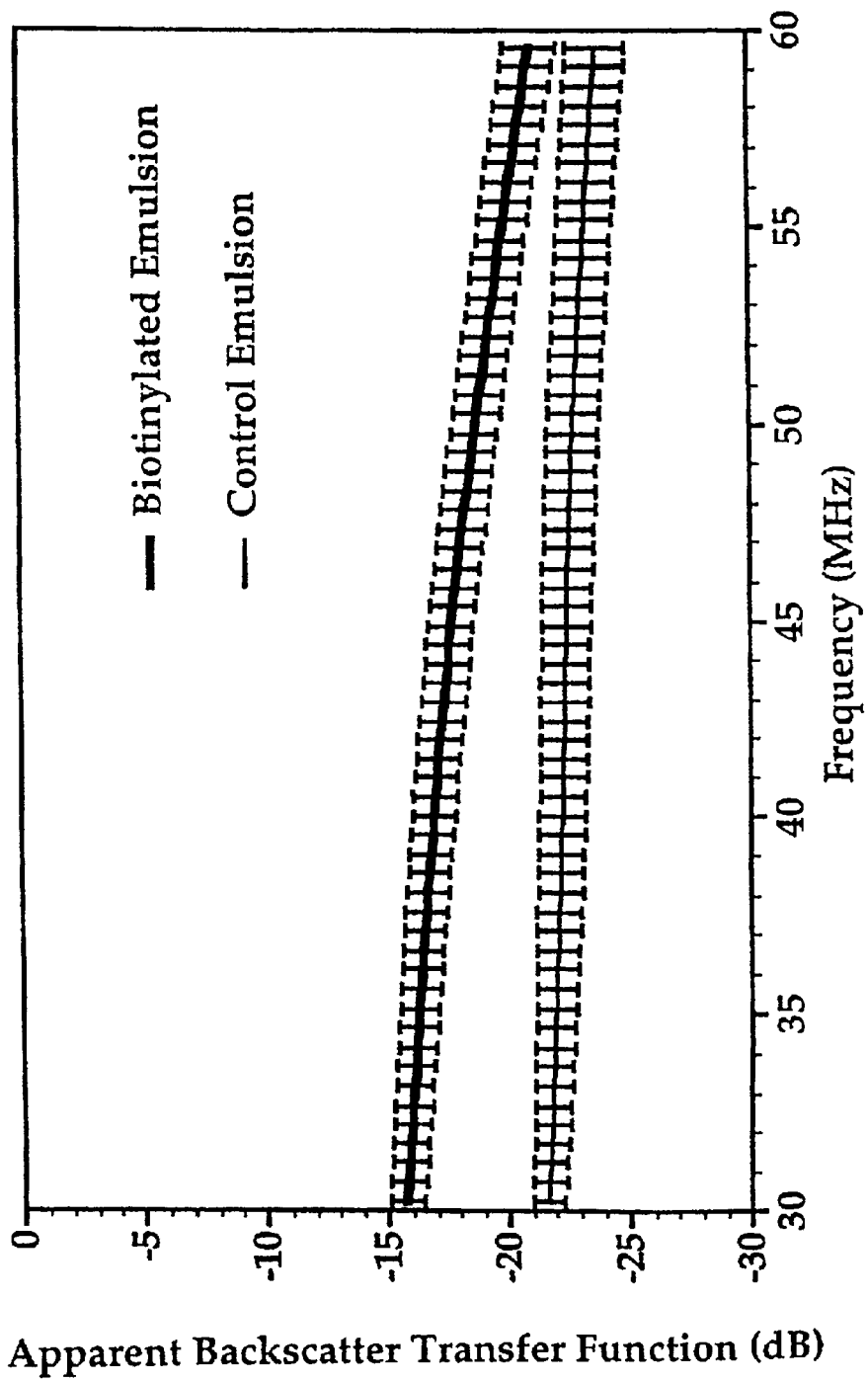
FIG. 6 Apparent Backscatter Transfer Function of Biotinylated and Control Perfluorocarbon Emulsions Targeted to D-dimer Covalently Conjugated to Nitrocellulose Membranes

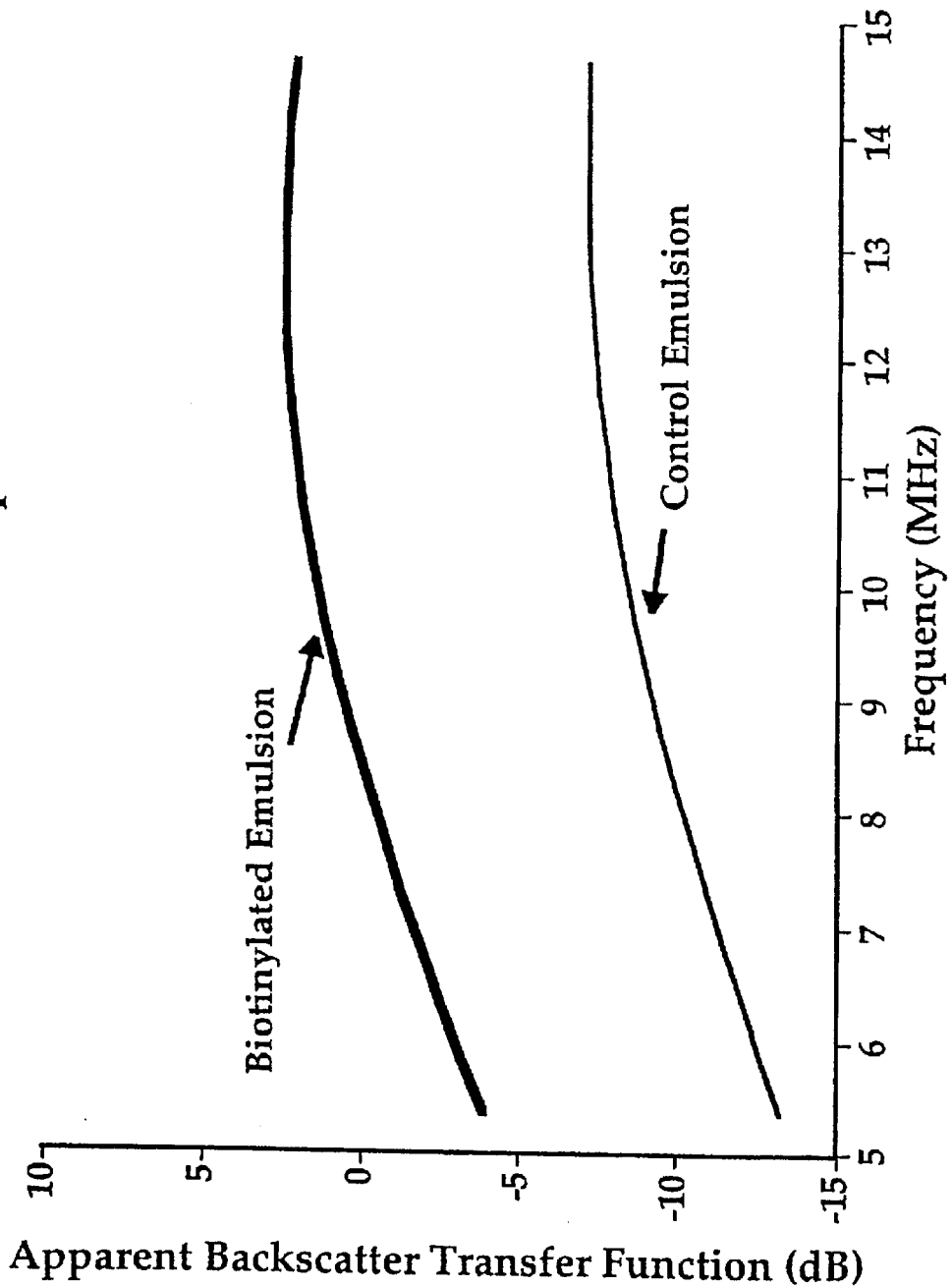
FIG. 7 Apparent Backscatter Transfer Function (dB) of Biotinylated and Control Perfluorocarbon Emulsions at Low Ultrasonic Frequencies

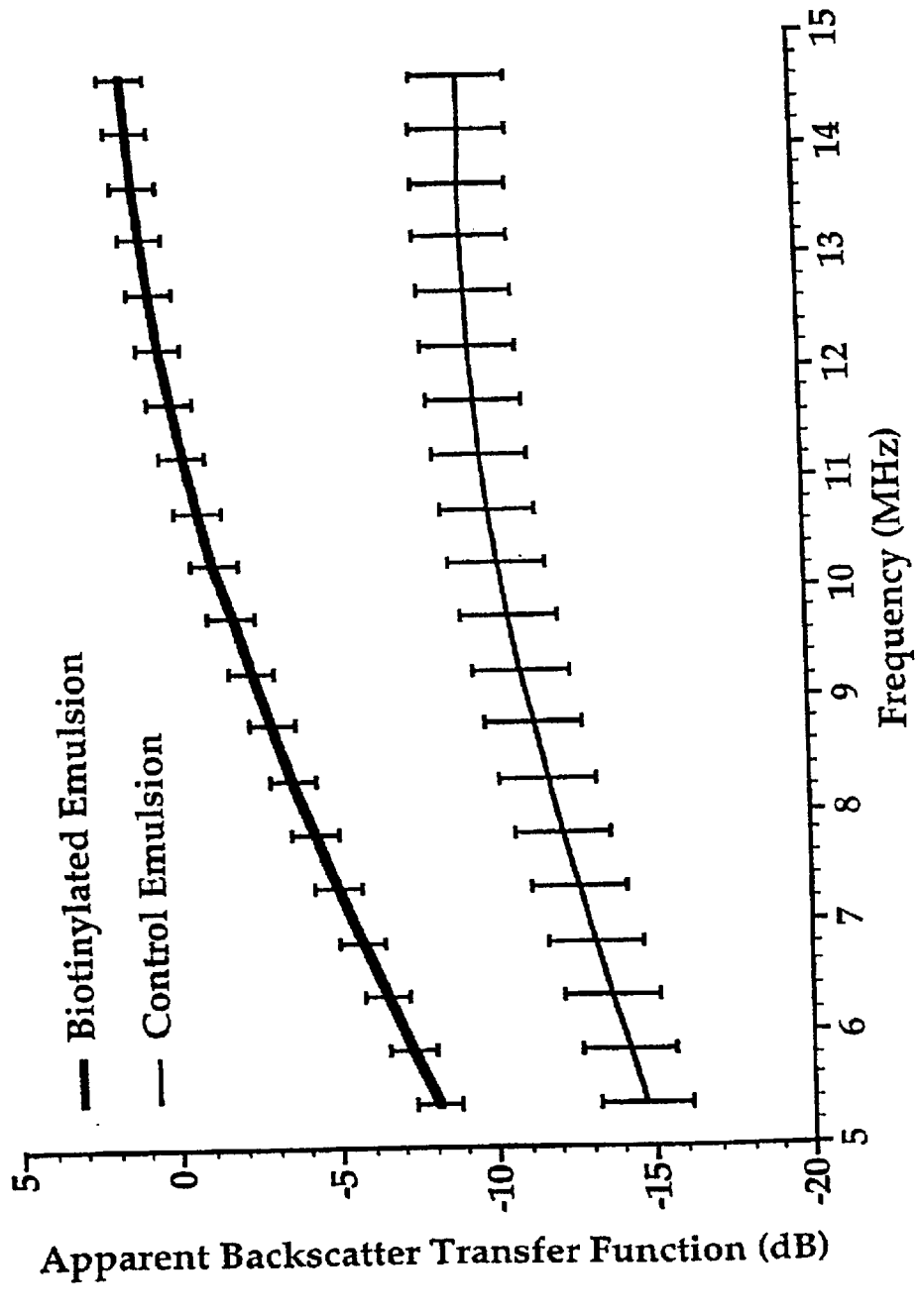
FIG. 8  Apparent Backscatter Transfer Function of Biotinylated and Control Perfluorocarbon Large Particle Size Emulsions Targeted to Avidinized

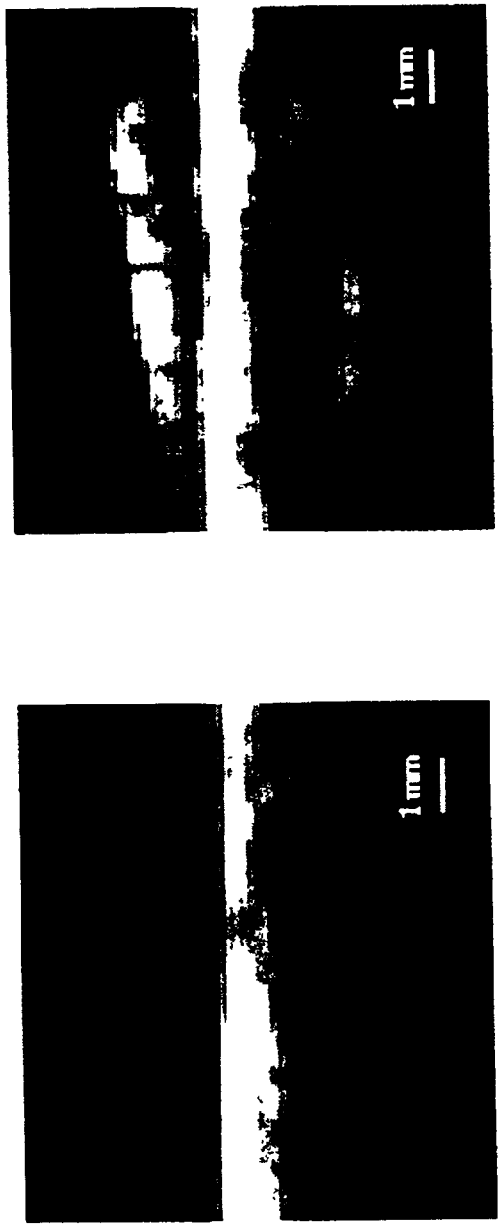
Figure 9. Ultrasonic Images (7.5 MHz) of Plasma Thrombi Pre-targeted with Antifibrin Monoclonal Antibody and Exposed to Control or Biotinylated Perfluorocarbon Emulsion *in Vitro*

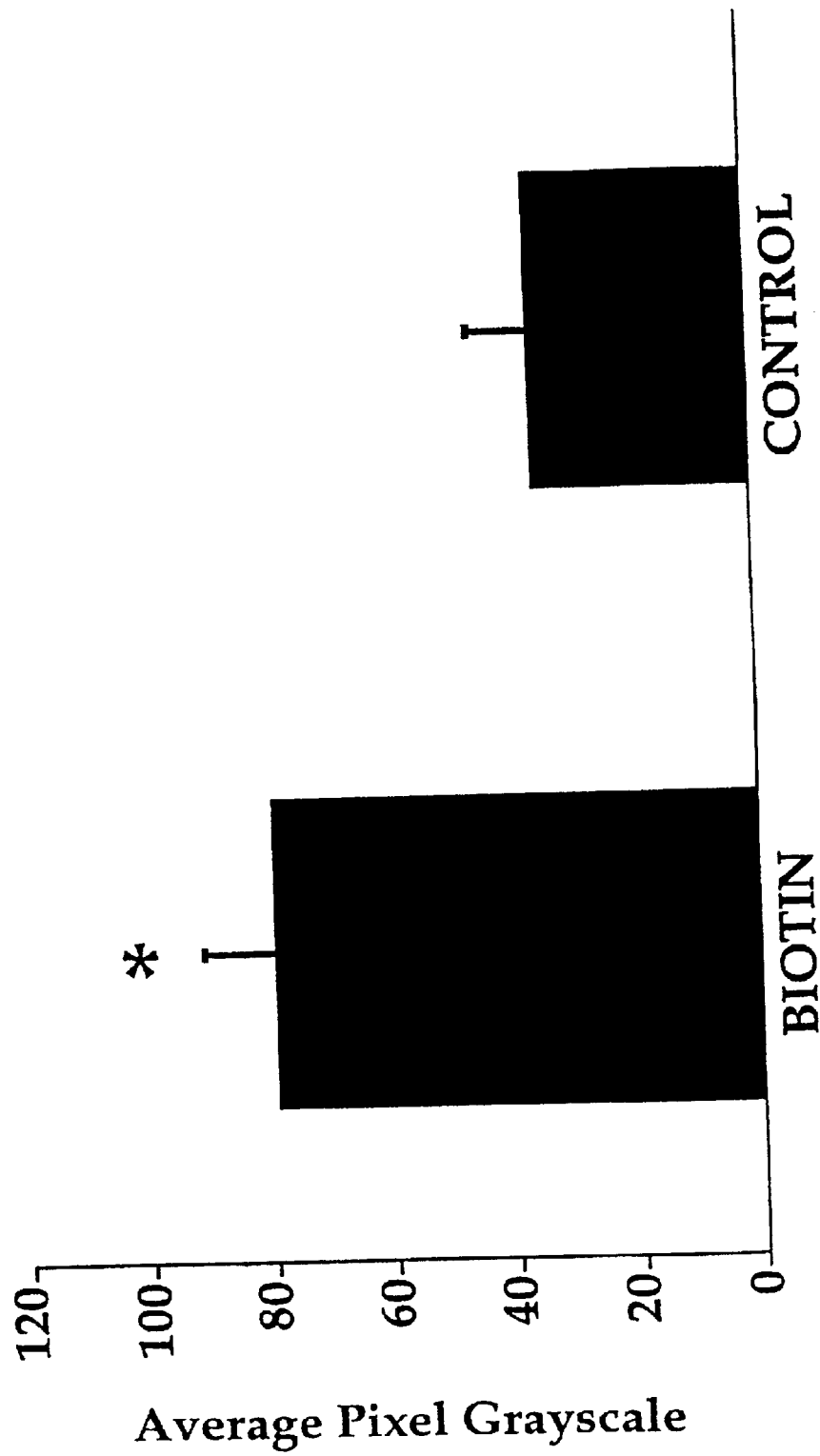
FIG. 10 Average Pixel Grayscale of Plasma Thrombi Pre-targeted with Antifibrin Monoclonal Antibody and Exposed to Control or Biotinylated Perfluorocarbon Emulsion

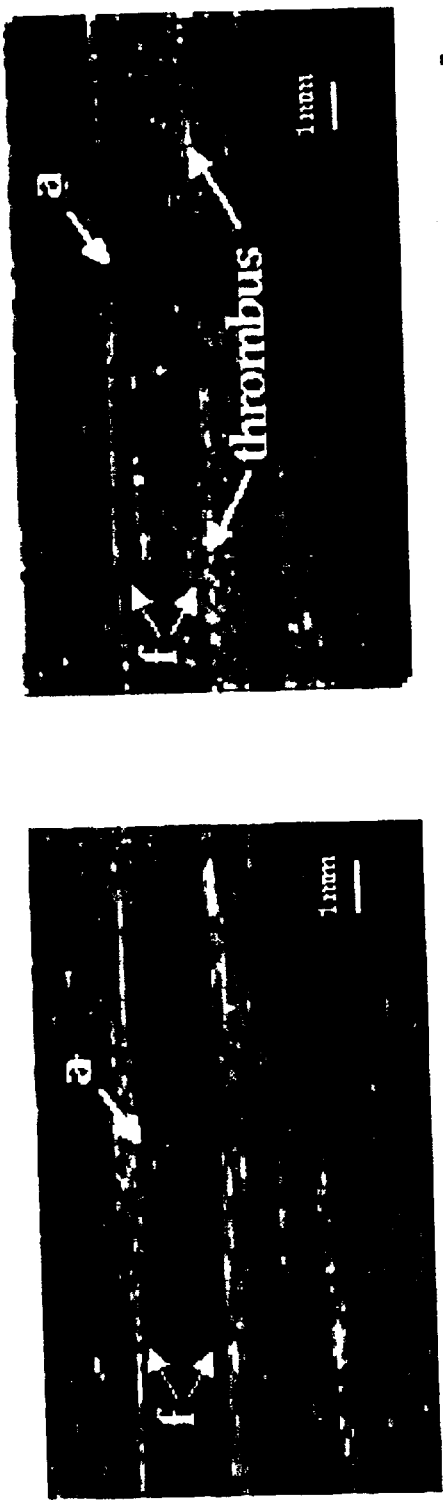
Figure 11. Femoral Artery Thrombus Acoustically Enhanced with Biotinylated Perfluorocarbon Emulsion *In Vivo*
Thrombus Before Targeted Biotinylated Contrast
Thrombus After Targeted Biotinylated Contrast
Imaged with HP Sonos 2500
7.5 MHz Focused, Linear Phased Array Transducer
Key: a=electrical anode; f=femoral artery walls

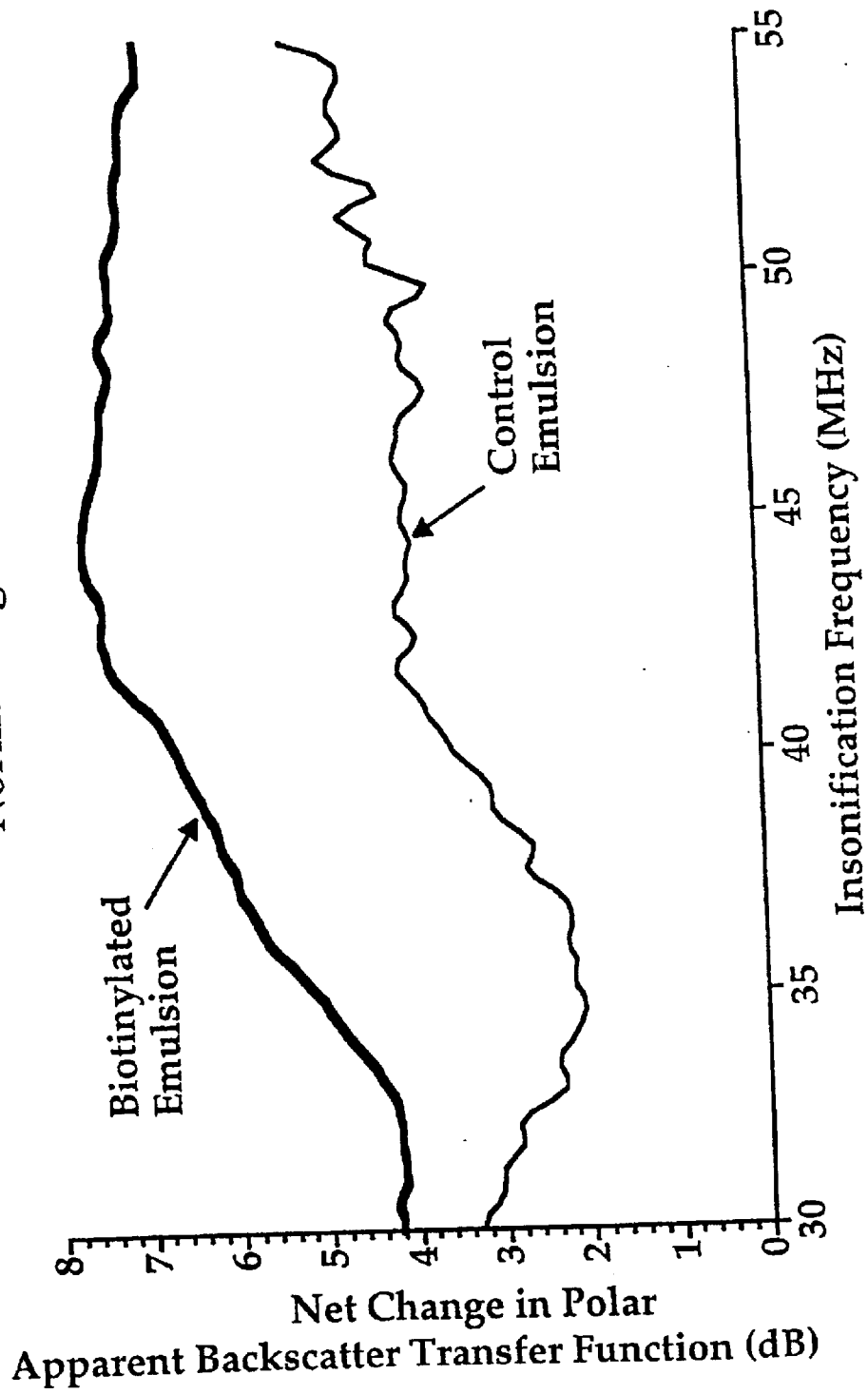
FIG. 12 Net Change in Apparent Backscatter Transfer Function of Biotinylated and Control Perfluorocarbon Emulsions Targeted to Prostate Specific Antigen in Prostatic Car

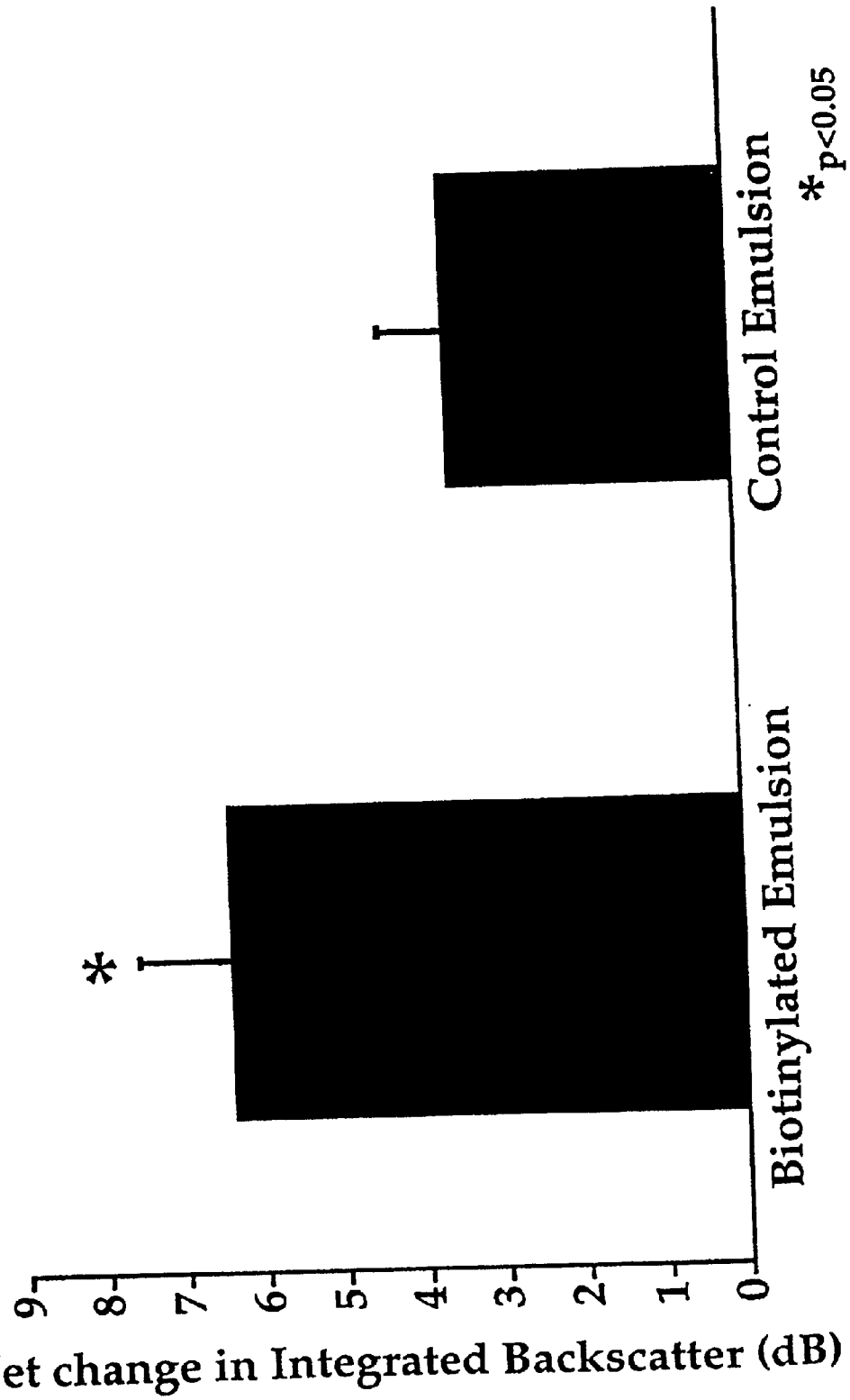
FIG. 13 Net Change in Integrated Backscatter between Normal Prostatic Stroma and Cancer Regions for Control versus Biotinylated Perfluorocarbon Emulsions

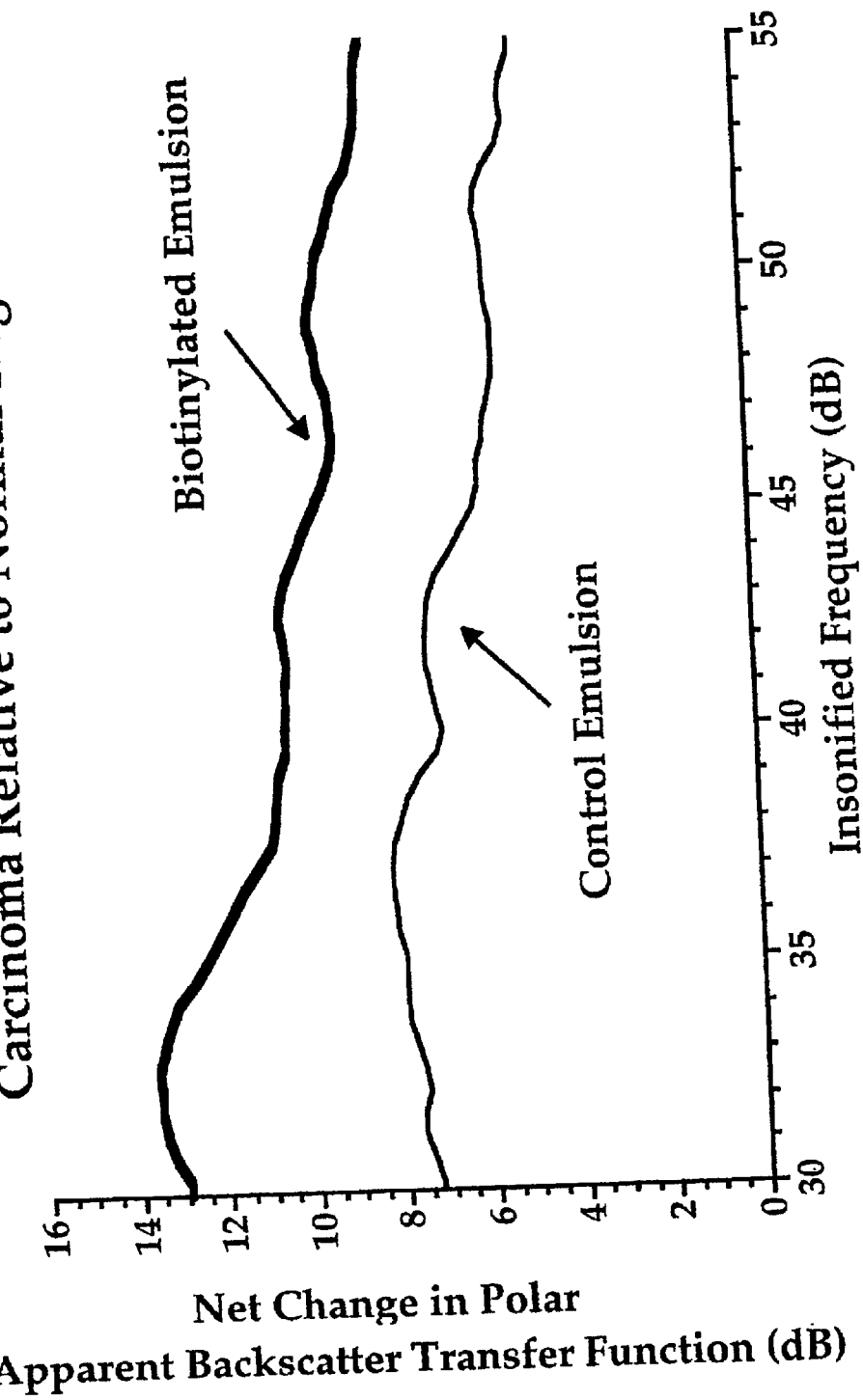
Net Change in Apparent Backscatter Transfer Function of Biotinylated and Control Perfluorocarbon Emulsions Targeted to OC-125 Antigen in Ovarian Carcinoma Relative to Normal Regions

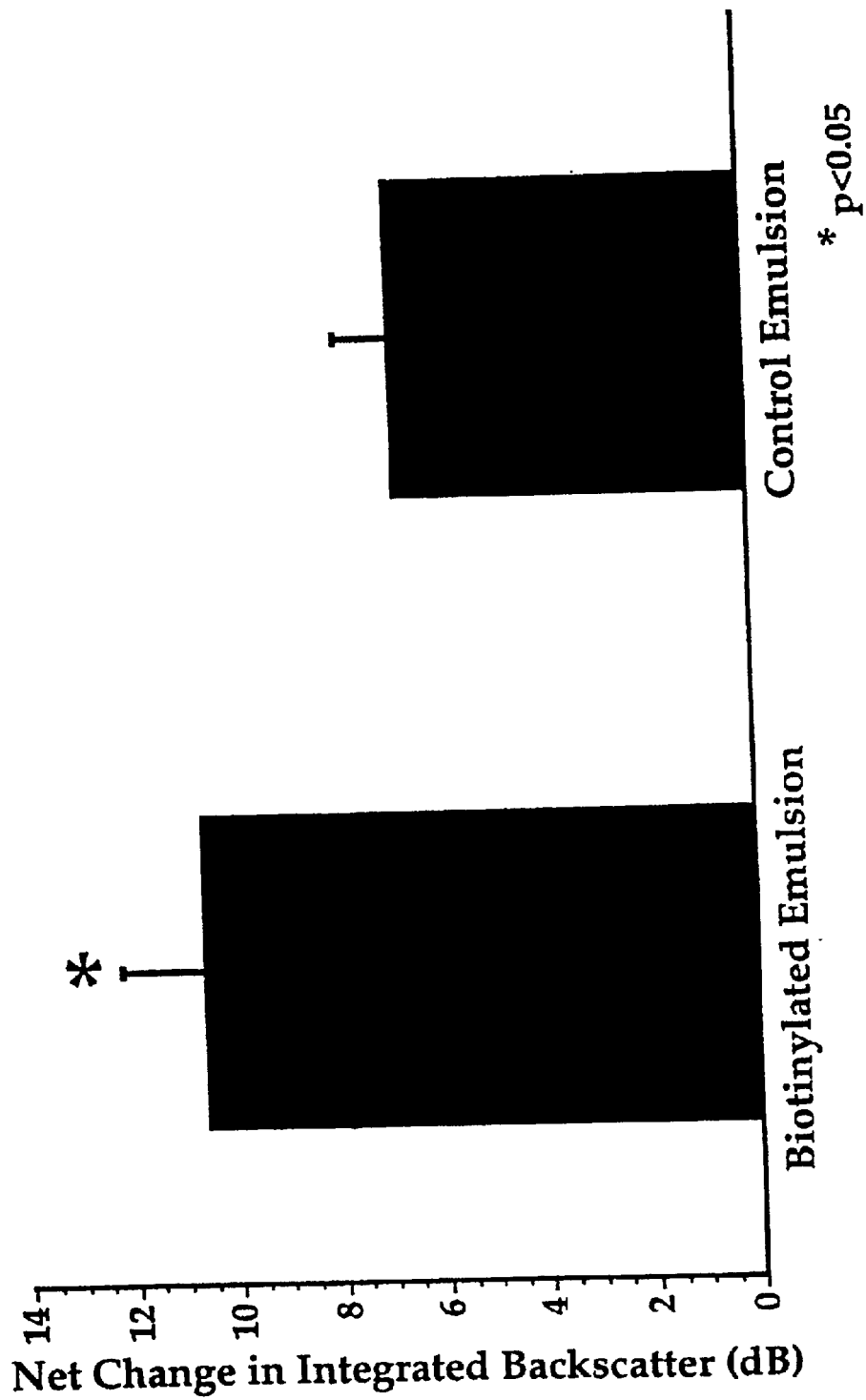
FIG. 15 Net Change in Integrated Backscatter Between Normal Ovarian Tissue and Carcinoma Regions for Control versus Biotinylated Perfluorocarbon Emulsions

Figure 16. Comparison of Ultrasonic and Optical Images of Tonsil Using Perfluorocarbon Contrast and Horseradish Peroxidase Targeted to Epithelium with Anticytokeratin Antibodies
Immunostained Tonsil
Peak Detected Image 100μm step size

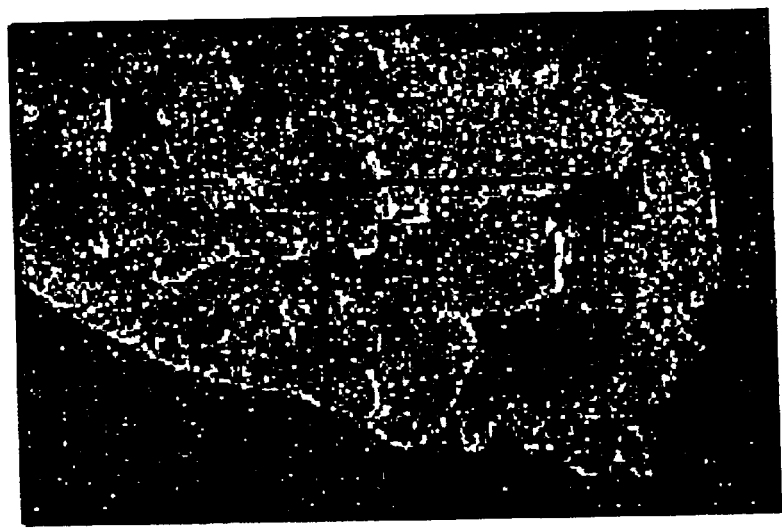
Figure 17. Peak Detected Ultrasonic Radiofrequency Images of Tonsil Epithelium Acoustically Enhanced with Anticytokeratin Antibody Targeted Perfluorocarbon Emulsion
Zoom: 50µ step size
Peak Detected Image 100µ Step Size FIG. 21
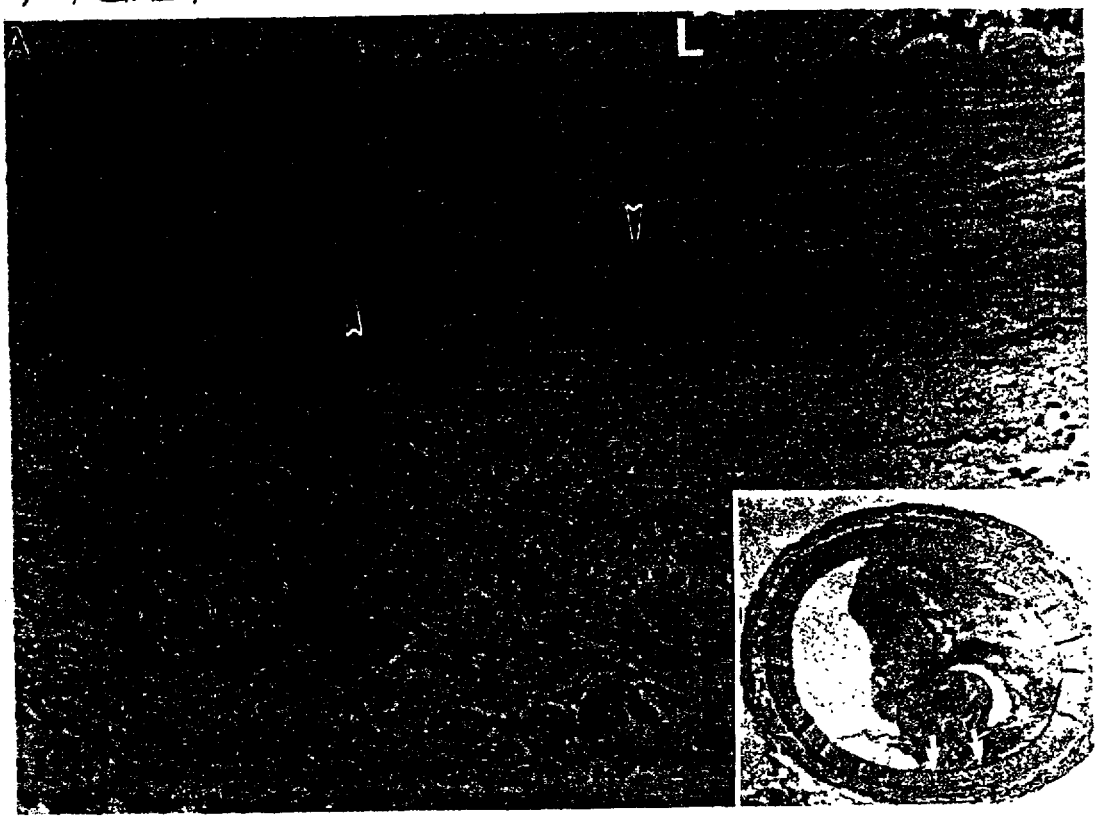
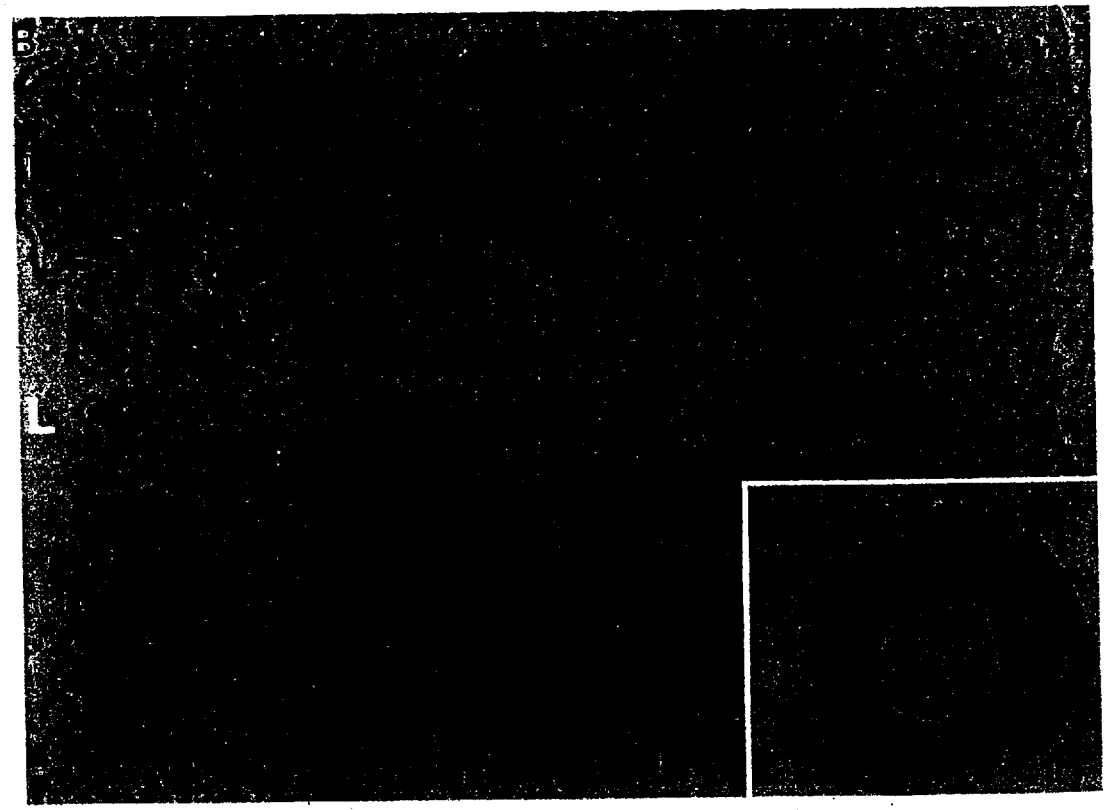

SITE SPECIFIC BINDING SYSTEM, IMAGING COMPOSITIONS AND METHODS

CROSS-REFERENCE TO RELATED APPLICATIONS

This application is a divisional application of U.S. Ser. No. 09/404,963, filed Sep. 24, 1999, and now U.S. Pat. No. 6,548,046 which is a continuation-in-part of U.S. Ser. No. 09/189,118, filed Nov. 9, 1998 and now abandoned which is a continuation of U.S. Ser. No. 08/854,308, filed May 12, 1997 and now abandoned which is a divisional of U.S. Ser. No. 08/488,743 filed Jun. 8, 1995, and now U.S. Pat. No. 5,690,907. The contents of these applications are incorporated herein by reference.

BACKGROUND OF THE INVENTION

This invention relates to a novel site specific binding system and novel compositions, and more particularly, to such a system and compositions which are useful in improved methods for ultrasonic imaging, drug or chemotherapeutic agent delivery, and diagnostic assays and detection systems.

Heretofore, with respect to ultrasonic imaging, although ultrasonic contrast agents based upon "bubble" technology have been demonstrated to develop an acoustic impedance mismatch by virtue of gas encapsulated either in protein (Feinstein et al., J. Am. Coll. Cardiol. 1990; 16:316–324 and Keller et al., J. Am. Soc. Echo. 1989; 2:48–52), polysaccharide (Corday et al., J. Am. Coll. Cardiol. 1984; 3:978–85) biodegradable polymers (Schneider et al., Invest. Radiol., 1993; 27:134–139 and Bichon et al., European Patent Application No. 8908103 67.4: 1990) or lipids (D'Arrigo et al., J. Neurormag., 1991; 1: 134139; Simon et al., Invest. Radiol., 1992; 27:29–34; and Unger et al., Radiology 1992; 195:453–456), no experimental evidence of site-specific targeting of an acoustic contrast or imaging agent with resultant changes in the acoustic properties of the targeted tissue, surface or support are known. This lack of results has occurred despite numerous methods described in the literature for modifying such agents for targeting purposes, and the failure of past targeting approaches may be due to the chemical nature of the agents, production process limitations or particle instabilities.

Nongaseous acoustic contrast agents have been described including lipid emulsions(Fink et al., Ultrason. Imaging, 1985 7:191–197) liposomes (Lanza et al., J. Am. Coll.Cardiol., 1992 (abstract); 19 (3 Suppl A) 114A), and perfluorocarbon emulsions (Mattrey et al., Radiology 1982; 145: 759–762 and Mattrey et al., Ultrasound Med. 1983; 2:173–176). As with the contrast agents discussed above, no demonstration of site targeted emulsion or liposome has been reported. Again, such failure may reflect instability of the particles, process incompatibilities or the chemical nature of the contrast agent. Lipid emulsions were evaluated by Fink et al. supra and did not exhibit adequate echogenicity in studies examining hepatic imaging. A unique chemical formulation of liposomes described by Lanza et al. supra was suggested to have the potential to be a targetable ultrasonic contrast but such has not been demonstrated to date. Perfluorocarbon emulsions, Perflubron (perfluorooctylbromide, P 100) and Flusol (perfluorodecalin and perfluorotripropylamine, F20) have been used as ultrasonic contrast agents and have been reported to accumulate in liver, spleen and tumors secondary to phagocytic uptake of emulsion particles at these sites (Mattrey et al. 1983, supra). These perfluorocarbon emulsions have also been noted to enhance Doppler signals and opacify lumens. Fluorocarbons and fluorocarbon emulsions for use as contrast agents are disclosed in U.S. Pat. Nos. 4,927,623, 5,077,036, 4,838,274, 5,068,098, 5,114,703, 5,362,477, 5,362,478, 5,171,755, 5,304,325, 5,350,571 and 5,403,575. However, no demonstration of perfluorocarbon emulsions as a ligand targeted acoustic contrast system has been reported.

Previous descriptions of tissue or organ targeting in biomedical ultrasonics has referred to the collection of acoustically reflective particles within or around structural tissue abnormalities. Localized acoustic enhancement of tissue pathologies (e.g. malignancies) has not been ligand-directed but rather has depended upon differential dynamic rates of particle uptake and/or clearance between normal and malignant tissues. Such contrast agents have included aqueous solutions (Ophir et al., Ultrason. Imaging 1979, 1:265–279; Ophir et al., Ultrasound Med. Biol. 1989, 15:319–333; and Tyler et al., Ultrason. Imaging, 3:323–329), emulsions (Fink et al. Ultrason. Imaging, 1985, 7:191–197), and suspensions (Mattrey et al. 1982 supra and Mattrey et al., Radiology, 1987, 163:339–343). Although the possibility of ligand-directed ultrasonic contrast targeting with acoustically reflective liposomes has been suggested, no successful applications of this concept have been reported (Lanza et al. 1992, supra and Valentini et al., J. Am. Coll. Cardiol., 1995, 25:16A). Previous approaches to targeting in vivo of particles have involved direct conjugation of a ligand (e.g. monoclonal antibody) to a vesicle by a variety of methods (see, for example, Torchlin et al., Biochem. Biophys. Res. Commun. 1978, 85:983–990; Endoh et al., J. Immunol. Methods, 1981, 44:7985; Hashimoto et al., J. Immunol. Methods, 1983, 62:155–162 and Martin et al., Biochemistry, 1981, 20:4229–4238).

There remains a need for new and improved methodologies for ligand-based binding systems which can be adapted as an ultrasonic contrast system permitting detection of molecular moieties such as peptides, carbohydrates or nucleic acids and whose uses can range from ultrasound-based ELISA-like laboratory diagnostic assays in liquid and solid phase systems and in cell cultures; electrophoretic, chromatographic and hybridization detection systems to the detection of thrombi, infections, cancers and infarctions in patients with the use of conventional ultrasonic imaging methods.

SUMMARY OF THE INVENTION

Among the several objects of the invention may be noted the provision of a novel method for ligand-based binding of lipid encapsulated particles to molecular epitopes on a surface in vivo or in vitro, the provision of such a method in which the ligand is conjugated to the lipid encapsulated particles through an avidin-biotin interaction and the resulting conjugate is bound to molecular epitopes on a surface; the provision of such a method which is useful for enhancing the acoustic reflectivity of a biological surface for ultrasonic imaging; the provision of a method of this type wherein the conjugate formed is effective for imaging by x-ray, ultrasound, magnetic resonance or positron emission tomography; the provision of compositions for use in ultrasonic imaging of a biological surface and for enhancing the acoustic reflectivity of such a surface; the provision of ultrasonic contrast agents which become highly reflective when bound to the desired site or biological surface through the ligand-based binding system of the invention; and the provision of such methods and compositions which are capable of targeting and altering the echogenic properties of a tissue surface for improved and specific identification of pathological processes. Other objects will be in part apparent and in part pointed out hereinafter.

Briefly, in its broadest embodiment, the present invention is directed to a method for ligand-based binding of lipid encapsulated particles to molecular epitopes on a surface in vivo or in vitro which comprises sequentially administering (a) a site-specific ligand activated with a biotin activating agent; (b) an avidin activating agent; and (c) lipid encapsulated particles activated with a biotin activating agent, whereby the ligand is conjugated to the particles through an avidin-biotin interaction and the resulting conjugate is bound to the molecular epitopes on such surface. The conjugate is effective for imaging by x-ray, ultrasound, magnetic resonance or positron emission tomography. In a more specific embodiment, the invention is directed to a method for enhancing the acoustic reflectivity of a biological surface through the sequential administration of the above-noted components whereby the resulting conjugate is bound to a natural or synthetic surface to enhance the acoustic reflectivity thereof for ultrasonic imaging. The invention is also directed to compositions for use in ultrasonic imaging of such surfaces and for enhancing the acoustic reflectivity thereof.

BRIEF DESCRIPTION OF THE DRAWINGS

FIG. 1 is a graph showing changes in aggregate particle size of biotinylated and control perfluorocarbon emulsions with increasing avidin concentration;

FIG. 2 shows ultrasonic images of control and biotinylated perfluorocarbon emulsion before and after the addition of avidin;

FIG. 3 is a graphic illustration of dialysis tubing images and region of interest placement for gray scale analysis;

FIG. 4 is a graph showing changes in average pixel gray scale associated with the addition of avidin to control or biotinylated perfluorocarbon emulsion;

FIG. 5 is a graph showing the effect of control and biotinylated perfluorocarbon emulsion on apparent backscatter transfer function and integrated backscatter of avidinized nitrocellulose membranes;

FIG. 6 is a graph showing the apparent backscatter transfer function of biotinylated and control perfluorocarbon emulsions targeted to D-dimer covalently conjugated to nitrocellulose membranes;

FIG. 7 is a graph showing the apparent backscatter transfer function (dB) of biotinylated and control perfluorocarbon emulsions at low ultrasonic frequencies;

FIG. 8 is a graph showing the apparent backscatter transfer function of biotinylated and control perfluorocarbon large particle size emulsions targeted to avidinized nitrocellulose membranes;

FIG. 9 shows ultrasonic images of plasma thrombi before and after exposure to control or biotinylated emulsions;

FIG. 10 is a graph showing the average pixel grayscale level of plasma thrombi pretargeted with antifibrin monoclonal antibody and exposed to control or biotinylated perfluorocarbon emulsion;

FIG. 11 shows ultrasonic images of femoral artery thrombus acoustically enhanced with biotinylated perfluorocarbon emulsion in vivo;

FIG. 12 is a graph showing the net change in apparent backscatter transfer function of biotinylated and control perfluorocarbon emulsions targeted to prostate specific antigen in prostatic carcinoma relative to normal regions;

FIG. 13 is a graph showing the net change in integrated backscatter between normal prostatic stroma and cancer regions for control versus biotinylated perfluorocarbon emulsions;

FIG. 14 is a graph showing the net change in apparent backscatter transfer function of biotinylated and control perfluorocarbon emulsions targeted to OC-125 antigen in ovarian carcinoma relative to normal regions;

FIG. 15 is a graph showing the net change in integrated backscatter between normal ovarian tissue and carcinoma regions for control versus biotinylated perfluorocarbon emulsions;

FIG. 16 shows ultrasonic and optical images of tonsil using perfluorocarbon contrast and horseradish peroxidase targeted to epithelium with anticytokeratin antibodies; and FIG. 17 shows peak detected ultrasonic images of tonsil epithelium acoustically enhanced with anticytokeratin antibody targeted perfluorocarbon emulsion.

FIG. 18 is a graph showing backscattered power from plasma clots after the one step fibrin targeted emulsion, the backscatter being computed from the average of the frequency-dependent backscatter transfer function over the useful bandwidth of the transducer;

FIG. 19 shows scanning electron microscope images of cell cultures treated with no (FIG. 19A) or untargeted control emulsion (FIG. 19B), tissue factor targeted specifically bound to the aortic smooth muscle cells (FIG. 19C) and binding specifically blocked by anti-tissue factor antiserum (FIG. 19D);

FIG. 20 shows ultrasonic images of vessels before and after treatment with targeted conjugated emulsion; and FIG. 21 shows the results of staining which revealed a pattern of localization of tissue factor in balloon-injured vessels in the media (arrows) at the site of acoustic contrast enhancement, as well as on the internal surface associated with inflammatory cells (FIG. 21 A; L-lumen) and control uninjured vessels exhibiting staining primarily on the adventitia and not in the tunica media (FIG. 21B).

DESCRIPTION OF THE PREFERRED EMBODIMENTS

In accordance with the present invention, it has now been found that a ligand-based binding system having broad application may be achieved through ligand-based binding of lipid encapsulated particles to molecular epitopes on a surface in vivo or in vitro by sequentially administering (a) a site-specific ligand activated with a biotin activating agent; (b) an avidin activating agent; and (c) lipid encapsulated particles activated with a biotin activating agent, whereby the ligand is conjugated to the lipid encapsulated particles through an avidin-biotin interaction or complexing and the resulting conjugate is bound to the molecular epitopes on the surface. The ligand-based binding system of the present invention thus permits detection of molecular moieties such as peptides, carbohydrates or nucleic acids with a specific ligand probe (e.g. an antibody or antibody fragment) complexed or conjugated with avidin and biotin, the latter being carried by lipid encapsulated particles (e.g. biotinylated lipid encapsulated emulsion or liposome). The ligand-based binding system of the invention may be employed in an ultrasonic contrast agent system, ultrasound-based ELISA-like laboratory diagnostic assays in liquid and solid phase systems and in cell cultures, electrophoretic, chromatographic and hybridization detection systems, and for the detection of thrombi, infections, cancers and infarctions in patients with the use of conventional ultrasonic imaging methods. The invention may also be applied for therapeutic purposes by delivery of chemotherapeutic agents or drugs to desired sites due to the specificity of the binding system coupled with the ability to monitor the progress of the therapeutic treatment through repeated imaging at such sites. In this regard, the above-referred to conjugate of the ligand to the lipid encapsulated particles through an avidin-biotin interaction or complexing is effective for imaging by x-ray, ultrasound, magnetic resonance or positron emission tomography.

In one embodiment of the invention, there is provided a method for enhancing the reflectivity of a biological surface by sequentially administering to the surface (a) a site-specific ligand activated with a biotin activating agent; (b) an avidin activating agent; and (e) lipid encapsulated particles activated with a biotin activating agent; whereby the ligand is conjugated to the lipid encapsulated particles through an avidin-biotin interaction and the resulting conjugate is bound to the biological surface to enhance the acoustic reflectivity thereof for ultrasonic imaging. This novel triphasic approach utilizes an avidin-biotin interaction to permit administration of the targeting ligand separate from the acoustic lipid encapsulated particles. In a specific application of the method in accordance with the invention, a biotinylated ligand is first systemically administered to a patient to pretarget the tissue or biological surface of interest and to circulate for a period of time necessary or sufficient to optimize the percentage bound. In the second phase, avidin is administered, circulates and binds to the biotinylated ligand attached to the target tissue or surface and to any residual, free circulating ligand. Avidin cross-linking increases the avidity and stability of the ligand on the target tissue or surface while promoting the rapid clearance of circulating avidin-ligand complexes via the reticuloendothelial system. In the third phase, the biotinylated lipid encapsulated particles are administered, binding to avidin through unoccupied biotin binding sites, and imparting increased acoustic contrast to the targeted tissue surface. Repeated sequential administration of avidin and the biotinylated lipid encapsulated particles may be carried out to amplify the acoustic contrast effect of the lipid encapsulated particles bound to the targeted surface.

In the practice of the invention, the ligand employed may be, for example, constituted by monoclonal or polyclonal antibodies, viruses, chemotherapeutic agents, receptor agonists and antagonists, antibody fragments, lectin, albumin, peptides, hormones, amino sugars, lipids, fatty acids, nucleic acids and cells prepared or isolated from natural or synthetic sources. In short, any site-specific ligand for any molecular epitope or receptor to be detected through the practice of the invention may be utilized.

The ligand is activated with a biotin activating agent. As employed herein, the term "biotin activating agent" or "biotinylated" encompasses biotin, biocytin and other biotin analogs such as biotin amido caproate N-hydroxysuccinimide ester, biotin 4-amidobenzoic acid, biotinamide caproyl hydrazide and other biotin derivatives and conjugates. Other derivatives include biotin-dextran, biotin-disulfide-N-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides and biotinylated amino acids such as Nε-biotinyl-l-lysine.

In the second phase, as previously mentioned, an avidin activating agent is administered. As employed herein, the term "avidin activating agent" or "avidinized" encompasses avidin, streptavidin and other avidin analogs such as streptavidin or avidin conjugates, highly purified and fractionated species of avidin or streptavidin, and non or partial amino acid variants, recombinant or chemically synthesized avidin analogs with amino acid or chemical substitutions which still accommodate biotin binding.

The lipid encapsulated particles or contrast agent employed in the third phase may be constituted, for example, by a biotinylated emulsion or liposome which may contain a gas, liquid or solid. In a specific example, the lipid encapsulated particles may be constituted by a perfluorocarbon emulsion, the emulsion particles having incorporated into their outer coating a biotinylated lipid compatible moiety such as a derivatized natural or synthetic phospholipid, a fatty acid, cholesterol, lipolipid, sphingomyelin, tocopherol, glucolipid, stearylamine, cardiolipin, a lipid with ether or ester linked fatty acids or a polymerized lipid. Thus, the biotinylated contrast agent constituting the lipid encapsulated particles may be produced by incorporating biotinylated phosphatidylethanolamine into the outer lipid monolayer of a perfluorocarbon emulsion.

Perfluorocarbon emulsions are particularly well suited for biomedical applications and for use in the practice of the present invention. They are known to be stable, biologically inert and readily metabolized, primarily by trans-pulmonic alveolae evaporation. Further, their small particle size easily accommodate transpulmonic passage and their circulatory half-life (4–8 hours) advantageously exceeds that of other agents. Also, perfluorocarbons have been used to date in a wide variety of biomedical applications, including use as artificial blood substitutes. For use in the present invention, various fluorocarbon emulsions may be employed including those in which the fluorocarbon is a fluorocarbon-hydrocarbon, a perfluoroalkylated ether, polyether or crown ether. Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorotributylamine, perfluorodecalin, perfluorooctylbromide, perfluorodichlorooctane, perfluorodecane, perfluorotripropylamine, perfluorotrimethylcyclohexane or other perfluorocarbon compounds. Further, mixtures of such perfluorocarbon compounds may be incorporated in the emulsions utilized in the practice of the invention. As a specific example of a perfluorocarbon emulsion useful in the invention may be mentioned a perfluorodichlorooctane emulsion wherein the lipid coating thereof contains between approximately 50 to 99.5 mole percent lecithin, preferably approximately 55 to 70 to mole percent lecithin, 0 to 50 mole percent cholesterol, preferably approximately 25 to 45 mole percent cholesterol and approximately 0.5 to 10 mole percent biotinylated phosphatidylethanolamine, preferably approximately I to 5 mole percent biotinylated phosphatidylethanolamine. Other phospholipids such as phosphatidylserine may be biotinylated, fatty acyl groups such as stearylamine may be conjugated to biotin, or cholesterol or other fat soluble chemicals may be biotinylated and incorporated in the lipid coating for the lipid encapsulated particles. The preparation of an exemplary biotinylated perfluorocarbon for use in the practice of the invention is described hereinafter in accordance with known procedures.

When the lipid encapsulated particles are constituted by a liposome rather than an emulsion, such a liposome may be prepared as generally described in the literature (see, for example, Kimelberg et al., CRC Crit. Rev. Toxicol. 6,25 (1978) and Yatvin et al., Medical Physics, Vol. 9, No. 2, 149 (1982)). Liposomes are known to the art and generally comprise lipid materials including lecithin and sterols, egg phosphatidyl choline, egg phosphatidic acid, cholesterol and alpha-tocopherol.

With respect to the particle size of the lipid encapsulated particles constituted by a perfluorocarbon emulsion or liposome, the particle size may range between approximately 0.05 to 5 microns and preferably between approximately 0.05 and 0.5 micron. Small size particles are thus preferred because they circulate longer and tend to be more stable than larger particles.

As indicated, the ligand is conjugated to the lipid encapsulated particles or perfluorocarbon emulsion through an avidin-biotin interaction. The ligand may also be conjugated to the emulsion directly or indirectly through intervening chemical groups or conjugated directly or indirectly to biotin or a biotin analog through intervening chemical groups such as an alkane spacer molecule or other hydrocarbon spacer. The use of spacer molecules between the ligand and biotin or between biotin and the emulsion is not required but aids in rendering the biotin more available for binding to avidin.

In accordance with the broadest aspect of the invention, it has been found that liquid perfluorocarbon emulsions have very poor intrinsic echogenicity when free in suspension, but when bound to a surface, they increase the acoustic reflectivity of the surface. By conjugating the ligand directly to the emulsion and binding the resulting ligand-emulsion conjugate to a surface, enhanced acoustic reflectivity is realized for ultrasonic imaging.

As previously mentioned, the emulsion or liposome constituting the lipid encapsulated particles or vesicles may contain a gas, liquid or solid. The gas may be nitrogen, oxygen, carbon dioxide or helium and may, for example, be evolved from the fluorocarbon component of the emulsions described above.

Alternatively, but less preferably, the ligand-based binding method of the invention may be carried out by sequentially administering a site-specific ligand activated with a biotin or avidin activating agent and lipid encapsulated particles activated with a biotin or avidin activating agent, a biotin activating agent being used where an avidin activating agent was employed in the first step and an avidin activating agent being used where a biotin activating agent was employed in the first step. The direct conjugation of the ligand to a perfluorocarbon emulsion, for example, is less preferable since it may accelerate in vivo clearance of the emulsion contrast agent.

In the practice of the invention, it has been unexpectedly found that the individual components of the ultrasonic contrast agents as described above are poorly reflective or have low echogenicity in the bloodstream but become highly reflective when the ligand-avidin-emulsion complex is formed in vivo at the desired site or biological surface and thereby substantially enhances the acoustic reflectivity thereof for ultrasonic imaging. This is in sharp contrast to previously known sonographic contrast agents which are inherently bright or of high reflectivity in the bloodstream. The improved acoustic reflectivity achieved through the present invention provides the advantage of enhancing the signal-to-noise ratio because the background contrast from lipid encapsulated particles in the blood is minimal. Thus, the present invention offers an improved noninvasive method for forming an acoustic contrast agent which can be targeted in vitro or in vivo and which when bound to a specific desired site alters the acoustic reflectivity of a tissue surface or support media in a manner detectable with ultrasonic transducers suitable for biomedical and diagnostic applications within a frequency range of at least 5 to 50 MHz (nominal center frequencies may be wider ranging based on the knowledge that these are broad band transducers). The method of the invention advantageously provides a practical means for detecting any molecular epitope or receptor for which a biotinylated monoclonal antibody or other ligand is available without the need for use of ionizing radiation with or without associated invasive procedures in various clinical applications and while employing standard, commercially available ultrasonic technology.

The present invention does not employ ultrasonic contrast systems or agents to delineate blood flow as in the prior art but rather to detect physiologic and pathologic events by sensing the accumulation of the contrast agent at specific binding sites.

In the application of the invention to diagnostic assays such as ultrasound-based ELISA-type laboratory diagnostic assays in liquid and solid phase systems, the surface on which ligand-based binding of lipid encapsulated particles to molecular epitopes occurs may be, for example, nylon, nitrocellulose membranes or a gel as well as a biological surface.

The ligand-based binding system of the invention may also be applied to provide a chemotherapeutic agent or gene therapy delivery system combined with ultrasonic imaging. For example, chemotherapeutic agents or immune activating drugs such as tissue plasminogen activator, adriarnycin, vincristine, urokinase, streptokinase, methotrexate, cytarabine, thioguanine, doxorubicin, 5-fluorouracil, cisplatin, etoposide, ifosfamide, asparginase, deoxycoformycin, hexamethyl melamine and including radioactive agents may be incorporated in the lipid encapsulated particles and become part of the conjugate bound to a specific biological surface site for therapeutic action. The present invention would also advantageously permit the site to be ultrasonically imaged in order to monitor the progress of the therapy on the site and to make desired adjustments in the dosage of therapeutic agent subsequently directed to the site. The invention thus provides a noninvasive means for the detection and therapeutic treatment of thrombi, infections, cancers and infarctions in patients while employing conventional ultrasonic imaging systems.

The following examples illustrate the practice of the invention.

EXAMPLE 1

The procedure for preparing a biotinylated lipid encapsulated perfluorodichlorooctane emulsion for use in ultrasound imaging is as follows.

The biotinylated lipid perfluorodichlorooctane (PFDCO) emulsion is comprised of the following components: PFDCO (40% v/v), safflower oil (2.0% w/v), a surfactant co-mixture (2.0% w/v) and glycerin (1.7% w/v). The surfactant co-mixture is composed of approximately 64 mole % lecithin, 35 mole % cholesterol and 1 mole % N-(6-biotinoyl)amino)hexanoyl)dipalmitoyl-L-alpha-phosatidylethano-lamine. These components are weighed together into a test tube and dissolved in chloroform. The chloroform is stripped from the material and the resulting surfactant mixture is dried in a 50° C. vacuum oven overnight. The co-mixture is dispersed into water by sonication resulting in a liposome suspension. The suspension is transferred into a 30 mL capacity blender cup (Dynamics Corporation of America, New Hartford, Conn.) along with the PFDCO and oil. The mixture is blended for 30–60 seconds to a pre-emulsion. The preemulsified sample is transferred to the reservoir of a microfluidizer, model S 110 (Microfluidics, Newton, Mass.), and emulsified for three minutes at 10,000 psi. To prevent the emulsion from heating excessively during homogenization, the shear valve and mixing coil of the microfluidizer are immersed in a room temperature water bath during processing. The final temperature of the emulsion is approximately 35° C. The finished emulsion is bottled in 10 mL serum vials, blanketed with nitrogen gas and sealed with stopper/crimp seal. The average particle size of the finished product, measured by a laser light scatter particle sizer (Brookhaven Instruments Corporation, Holtsville, N.Y.), is 250 nm.

EXAMPLE 2

The incorporation of biotinylated phosphatidylethanolamine into the encapsulating lipid monolayer of perfluorocarbon emulsion is prepared as described in Example one and demonstrated to increase aggregate particle size in the presence of titrated concentrations of avidin (Pierce, Rockford, Ill. 61105). An identically prepared control emulsion is prepared which incorporates nonbiotinylated phosphatidylethanolamine into the outer lipid monolayer of the perfluorocarbon emulsion. Avidin is resuspended in isotonic phosphate buffered saline (PBS, Fisher Inc., Fair Lawn, N.J.). Within a polystyrene cuvette, a 3.0 ml reaction mixture is prepared containing PBS, biotinylated or control perfluorocarbon emulsion (20 μl) and avidin, at 0.0, 0.5, 1.0, 1.5 or 2.0 μg/ml. Contents are mixed by gentle inversion and react for thirty minutes at room temperature. Emulsion particle sizes are determined in triplicate with a Brookhaven BI-90 particle size analyzer (Holtsville, N.Y.) at 37° C. Aggregate particle size of the biotinylated emulsion increased progressively from a baseline of 263±2.54 nm to greater than 2000 nm with increasing concentration of avidin (FIG. 1). Marked flocculation and sedimentation are noted when avidin concentrations exceed 2.0 μ/ml. The particle size of the control emulsion is 234±3.81 nm in diameter and addition of 2.0 μg of avidin to the reaction mixture does not affect particle size. These results clearly demonstrate that the biotinylated phosphatidylethanolarnine is incorporated and oriented appropriately into the outer lipid monolayer of the perfluorocarbon emulsion and that surface biotins are adequately available to avidin in the media. Multiple biotin binding sites on the avidin molecule as well as multiple biotin residues on the surface of the emulsion progresses towards a rapid complexing of particles in vitro.

EXAMPLE 3

Biotinylated perfluorocarbon emulsion particles, approximately 250 nm in diameter, with low independent acoustic reflectivity, are complexed with avidin in solution which eventuates aggregation and enhances echogenicity. Biotinylated and control perfluorocarbon emulsion (200 μl) prepared as described previously are diluted in PBS (15 ml) and placed within dialysis tubing (Spectra/Por 4, 25 mm, MWCO 12,000–14,000, Spectrum Medical Industries, Inc., Los Angeles, Calif.), ultrasonically imaged within a PBS water bath at room temperature using a 7.5 MHz focused transducer and a Hewlett Packard (HP) Sonos 2500 Phased Array Imaging System (Andover, Mass.). Real-time images are recorded to SVHS video tape for subsequent image analysis. Pixel grayscale and homogeneity are assessed on selected freeze-frame images using NIH Image 1.47 (National Institutes of Health). Avidin (30 μ/ml) is added to each emulsion suspension, mixed by gentle inversion and allowed to complex for 30 minutes. The emulsion suspensions are optically opaque but ultrasonically undetected prior to the addition of avidin. Complexing of the biotinylated perfluorocarbon emulsion ensues rapidly with the addition of avidin and a white, flocculant precipitate soon appears. Avidin induces no changes in control emulsion suspension. Insonification of the suspensions reveals that the biotinylated perfluorocarbon emulsion particles opacify the dialysis tubing; whereas, the control particles are not appreciated acoustically (FIG. 2). Gray scale echo intensity analysis of freeze-frame images of the control and biotinylated emulsion suspensions before and after avidin are summarized in FIGS. 3 and 4. The increased average grayscale level of the biotinylated emulsion (71.3±22.1) suspension relative to its pre-avidin pixel gray scale level (2.2±4.4) demonstrates the acoustic enhancement achieved. Average pixel gray scale levels of the control emulsion before (3±7.33) and after (1.0–+1.3) avidin addition are similar. These results demonstrate the low acoustic reflectivity of the perfluorocarbon emulsion when imaged as independent particles in comparison with the enhanced echogenic nature of the aggregated biotinylated particles. The lack of acoustic change in the control emulsion suspension in the presence of avidin confirms the ligand specificity of the biotinylated emulsion.

EXAMPLE 4

Biotinylated perfluorocarbon emulsion, approximately 250 nm diameter, are specifically targeted to avidin, covalently bound to a modified nitrocellulose membrane and increases the acoustic reflectivity of the membrane surface at high ultrasonic frequencies (30 to 60 MHz). Briefly, nitrocellulose membranes (S+S NCTM, Schleicher & Schuell, Keane, N.H.) were conjugated to avidin using a diaminohexane (Sigma Chemical Co., St. Louis, Mo.) spacer and glutaraldehyde (Sigma Chemical Co., St. Louis, Mo.) activation as described by Másson et al. (Electrophoresis 1993, 14, 860–865). Nitrocellulose discs (2 cm diameter) are soaked in 2.5% diaminohexane dissolved in deionized water for 60 minutes with constant slow rotary agitation. Membranes are washed with 1M acetic acid for 6–7 hours followed by an 18+ hour deionized water wash with constant agitation. The membranes are placed in 1% glutaraldehyde in 0.1 M sodium bicarbonate buffer, pH 10.0 for 15 minutes then washed for three hours with deionized water. Nitrocellulose membranes are stored and dried at 4° C. until use; storage does not exceed three days. Fifty (50) μl of avidin (250 μg) are spotted dropwise upon the center of six membranes with a microliter syringe and allowed to dry. Each membrane is extensively washed with a 0.1% Tween-20 (Sigma Chemical Co., St. Louis, Mo.) in PBS then placed in 3% bovine serum albumin (BSA, crystallized, Sigma Chemical Company, St. Louis, Mo.) dissolved in PBS-0.1% Tween-20 for 20 minutes to blockade nonspecific protein binding sites around the periphery of the disc. After the BSA blockade, each disc is extensively washed with PBS and placed in 300 μl of either biotinylated or control perfluorocarbon emulsion suspended in 4 ml PBS for 20 minutes. Unbound emulsion is removed in serial PBS washes. Each disc is reexposed to avidin and control or biotinylated emulsion to ensure saturated coverage of the nitrocellulose surface. The nitrocellulose discs are washed and stored in PBS at 4° C. until imaged with acoustic microscopy.

For acoustic microscopic imaging, each nitrocellulose disc is placed flat above a polished stainless steel plate in a polystyrene holder with a 2×2 cm central window removed. The mounted specimen is immersed into PBS at ambient temperature for ultrasonic insonification. A custom designed acoustic microscope, utilizing a 50 MHz (nominal frequency) broadband, focused, piezoelectric delay-line transducer (¼ inch diameter, ½ inch focal length, Model V390, Panametrics Co., Waltham, Mass.) operated in the pulse-echo mode is utilized for insonification. Backscattered radio frequency (RF) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 100 micron lateral step resolution.

A radio frequency peak-detected scan of the data is converted into a gray scale (O=lowest scattering, 255=highest scattering) map to allow selection of regions of interest for integrated backscatter analysis. Radio frequency (RF) ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency dependent backscatter transfer function across the useful bandwidth of the transducer (30 to 60 MHz) are computed and expressed in decibels relative to acoustic scattering from the near perfect steel plate reflector (Wong et al., Ultrasound in Med & Biol. 1993; 19: 365–374). Integrated backscatter (IB) is computed as the average of the frequency-dependent backscatter transfer flnction across the useful bandwidth of the transducer.

Discs incubated with biotinylated perfluorocarbon emulsion have central regions with high acoustic scattering in comparison with the peripheral (i.e. background) regions of the same disc. Nitrocellulose discs incubated with the control emulsion have no central high scattering regions and no differences in acoustic character is detected by changes in the RF signature between the central and peripheral regions of the disc. IB from the centrally located, biotinylated emulsion region (−17.8±0.2 db) is 6.3±0.1 dB(4-fold) greater ($p<0.05$) than IB from the analogous region on the control disc (−24.1±0.2 dB). The frequency-dependent variation in apparent backscatter transfer function (mean±SEM) from the avidin spotted regions of the biotinylated and control emulsion discs are presented in FIG. 5. A smooth and consistently greater acoustic response is noted across the frequency spectrum due to the bound biotinylated emulsion. These results demonstrate the effectiveness of the biotinylated perfluorocarbon emulsion to specifically target a surface bound antigen and dramatically alter the acoustic reflectivity of the surface with the bathing medium, increasing the ultrasonic backscattered power at high frequencies.

EXAMPLE 5

Biotinylated perfluorocarbon emulsion (250 nm diameter) is specifically targeted to D-dimer covalently attached to a modified nitrocellulose membrane utilizing a biotinylated anti-D-dimer $F_{(ab)}$ fragment-avidin complex and results in a marked increase in the acoustic power reflected from the surface. D-dimer is covalently linked to nitrocellulose discs modified with a diaminohexane spacer arm and activated with glutaraldehyde as previously described in Example 4. Fifty (50) μg of D-dimer is spotted with a microliter syringe upon the center of three of six membranes and allowed to air dry. Unbound D-dimer is exhaustively washed from the membranes with phosphate buffered saline (PBS)-0.1% Tween-20. Nonspecific protein binding sites of all membranes are blocked with 3% bovine serum albumin (BSA) in PBS-0. I% Tween-20 for 20 minutes followed by serial PBS washes. D-dimer spotted membranes are incubated with 12.5 μg biotinylated anti-D-dimer F(ab) antibody in 4.0 ml 3% BSA for 2 hours, washed with PBS buffer and then incubated with 250 μg avidin in 4 ml PBS for 30 min. After removing unbound avidin with PBS washes, the discs are exposed to either biotinylated or control perfluorocarbon emulsion (300 μl) in 4.0 ml PBS for 20 minutes. Excess emulsion is removed with PBS buffer washes. Discs are reexposed to avidin and perfluorocarbon emulsion as described above and the membranes are stored in PBS at 4° C. until imaging.

For acoustic microscopic imaging, each nitrocellulose disc is placed flat above a polished stainless steel plate in a polystyrene holder, immersed in PBS at ambient temperature, and insonified with a custom designed acoustic microscope, utilizing a 50 MHz (nominal frequency) broadband, focused, piezoelectric delay-line transducer (¼ inch diameter, ½ inch focal length, Model V390, Panametrics Co., Waltham, Mass.) operated in the pulse-echo mode. Backscattered radio frequency (R.F) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 100 micron lateral step resolution.

A radio frequency peak-detected scan of the data is converted into a gray scale (0=lowest scattering, 255=highest scattering) map of the disc to allow visual inspection and selection of regions of interest for integrated backscatter (IB) analysis. Radio frequency (RF) ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (30 to 60 MHz) are computed and expressed in decibels relative to acoustic scattering from the near perfect steel plate reflector (Wong et al., Ultrasound in Med & Biol. 1993; 19: 365–374). Integated backscatter is computed as the average of the frequency-dependent backscatter transfer function across the useful bandwidth of the transducer.

Biotinylated, anti-D-dimer F(ab) fragment is specifically bound to the central region of the D-dimer spotted discs and crosslinked by avidin through its biotin moiety. As in previous examples, biotinylated perfluorocarbon emulsion specifically binds to the antibody bound avidin; whereas, the nonspecific binding of the control emulsion have no binding and are not detected acoustically. IB of the biotinylated emulsion coated nitrocellulose (−18.0±0.2 dB) was greater by 4.6±0.1 dB ($p<0.05$) than that from the control disc (−22.6±0.1 dB) over the 30 to 60 MHz frequency range. The frequency-dependent variation in apparent backscatter transfer function (mean±SEM) of the biotinylated and control emulsion discs are presented in FIG. 6. A smooth and consistently greater acoustic response is noted across the frequency spectrum due to the bound biotinylated emulsion. These data confirm and extend the findings of Example 4 with avidin alone, demonstrating that biotinylated perfluorocarbon emulsion bound through a specific, targeting ligand system can significantly enhance the acoustic backscatter of a solid support surface.

EXAMPLE 6

Biotinylated perfluorocarbon emulsion (250 nm diameter) is specifically targeted to avidin conjugated to nitrocellulose discs and insonified at clinically relevant frequencies (5 to 15 MHz) and significantly increases the acoustic backscatter of the membrane. Briefly, nitrocellulose membranes (S+S NCTM, Schleicher & Schuell, Keane, N.H.) are conjugated to avidin using a diaminohexane (Sigma Chemical Co., St. Louis, Mo.) spacer and glutaraldehyde (Sigma Chemical Co., St. Louis, Mo.) activation as described by Másson et al. (Electrophoresis 1993, 14, 860–865). Nitrocellulose discs (2 cm diameter) are soaked in 2.5% diaminohexane dissolved in deionized water for 60 minutes with constant, slow rotary agitation. Membranes are transferred to and washed with 1M acetic acid for 6–7 hours then transferred for continued washing in deionized water for at least 18 additional hours with constant agitation. The membranes are placed in 1% glutaraldehyde in 0.1M sodium bicarbonate buffer, pH 10.0 for 15 minutes. After glutaraldehyde activation is complete, the membranes are washed with continued agitation for three hours. The nitrocellulose membranes stored and dried at 4° C. until use; storage does not exceed three days. Fifty (50) $\mu$l of avidin (250 $\mu$g) are spotted dropwise upon the center of a nitrocellulose membrane with a microliter syringe and allowed to dry. Each membrane is washed with 0.1% Tween-20 (Sigma Chemical Co., St. Louis, Mo.) in phosphate buffered saline (PBS) then placed in 3% bovine serum albumin (BSA, crystallized, Sigma Chemical Company, St. Louis, Mo.) dissolved PBS-0.1% Tween-20 for 20 minutes to blockade nonspecific protein binding sites around the periphery of the disc. After the BSA blockade, each disc is washed with PBS and placed in 300 $\mu$l of either biotinylated or control perfluorocarbon emulsions suspended in 4 ml PBS for 20 minutes with mild, rotary agitation. The unbound emulsion is removed with washes of PBS. Each disc is reexposed to avidin, washed with PBS, reexposed to control or biotinylated perfluorocarbon emulsion and rewashed with PBS as previously described. The nitrocellulose discs are stored in PBS at 4° C. until imaged with the acoustic microscope.

For acoustic microscopic imaging, each nitrocellulose disc is placed flat above a polished stainless steel plate in a polystyrene holder with a 2 cm×2 cm central window removed. The mounted specimen is immersed into PBS at ambient temperature for ultrasonic insonification. A custom designed acoustic microscope, utilizing a 10 MHz (nominal frequency) broadband, focused, piezoelectric delay-line transducer (½ inch diameter, 2 inch focal length, Model V31 1, Panametrics Co., Waltham, Mass.) operated in the pulse-echo mode is utilized for insonification. Backscattered radio frequency (RF) data is collected and digitized at 500 megasamples per second utilizing a Tektronix DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 250 micron lateral step resolution. A radio frequency peak-detected scan of the data is converted into a gray scale (0=lowest scattering, 255= highest scattering) map of the disc to allow visual inspection and selection of regions of interest for integrated backscatter analysis. Radio frequency ultrasonic data are stored in a raster scan format and analyzed with custom software. Segments of the RF lines are gated for integrated backscatter analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (5 to 15 MHz) are computed and expressed in decibels relative to acoustic scattering from the near perfect steel plate reflector (Wong et al., Ultrasound in Med & Biol. 1993; 19: 365–374). Integrated backscatter (IB) is computed as the average of the frequency-dependent backscatter transfer function across the useful bandwidth of the transducer.

Discs incubated with biotinylated perfluorocarbon emulsion have central regions with high acoustic scattering relative to the peripheral regions of the same disc or the central regions of the control emulsion disc. Nitrocellulose discs incubated with the control emulsion have no high scattering regions. IB of the biotinylated emulsion coated nitrocellulose (0.5±0.5 dB) was greater by 9.6±0.1 dB (8-fold) ($p<0.05$) than that from the control disc (−9.2±0.5 dB) over the 5 to 15 MHz frequency range. The frequency-dependent variation in apparent backscatter transfer function (mean±SEM) of the biotinylated and control emulsion discs are presented in FIG. 7. A smooth and consistently greater acoustic response is noted across the frequency spectrum due to the bound biotinylated emulsion. These data confirm and extend the findings of Examples 4 and 5 with avidin and D-dimer, demonstrating that biotinylated perfluorocarbon emulsion bound through a specific, targeting ligand system can significantly enhance the acoustic backscatter of a solid support surface and that this improved acoustic backscatter is detected at low, clinically useful ultrasonic frequencies (5 to 15 MHz) as well as high frequencies (30 to 60 MHz).

EXAMPLE 7

Biotinylated perfluorocarbon contrast, approximately 3000 nm diameter, is specifically targeted to avidin conjugated to nitrocellulose discs and insonified at clinically relevant frequencies (at least 5 to 15 MHz bandwidth). Briefly, nitrocellulose membranes (S+S NCTM, Schleicher & Schuell, Keane, N.H.) are conjugated to avidin using a diaminohexane (Sigma Chemical Co., St. Louis, Mo.) spacer and glutaraldehyde (Sigma Chemical Co., St. Louis, Mo.) activation as described by Másson et al. (Electrophoresis 1993, 14, 860–865). Nitrocellulose discs (2 cm diameter) are soaked in 2.5% diaminohexane dissolved in deionized water for 60 minutes with constant, slow rotary agitation. Membranes are transferred to and washed with 1M acetic acid for 6–7 hours then transferred for continued washing in deionized water for at least 18 additional hours with constant agitation. The membranes are placed in 1% glutaraldehyde in 0.1 M sodium bicarbonate buffer, pH 10.0 for 15 minutes. After glutaraldehyde activation is complete, the membranes are washed with continued agitation for three hours. The nitrocellulose membranes stored and dried at 4° C. until use; storage does not exceed three days.

Fifty (50) $\mu$l of avidin (250 $\mu$g) are spotted dropwise upon the center of two of four membranes with a microliter syringe and allowed to dry. Each membrane is washed with 0.1% Tween-20 (Sigma Chemical Co., St. Louis, Mo.) in phosphate buffered saline (PBS) then placed in 3% bovine serum albumin (BSA, crystallized, Sigma Chemical Company, St. Louis, Mo.) dissolved PBS-0.1% Tween-20 for 20 minutes to blockade nonspecific protein binding sites around the periphery of the disc. After the BSA blockade, each disc is washed with PBS and placed in 300 $\mu$l of either biotinylated or control perfluorocarbon emulsions, approximately 3000 nm particle size, suspended in 4 ml PBS for 20 minutes with mild, rotary agitation. The unbound emulsion is removed with washes of PBS. Each disc is reexposed to avidin, washed with PBS, exposed to perfluorocarbon emulsion and rewashed with PBS as previously described. The nitrocellulose discs are stored in PBS at 4° C. until imaged with the acoustic microscope.

For acoustic microscope imaging, each nitrocellulose disc is placed flat above a polished stainless steel plate in a polystyrene holder with a 2 cm×2 cm central window removed. The mounted specimen is immersed into PBS at ambient temperature for ultrasonic insonification. A custom designed acoustic microscope, utilizing a broadband 10 MHz (nominal frequency) focused, piezoelectric delay-line transducer (½ inch diameter, 2 inch focal length, Model V31 1, Panametrics Co., Waltham, AM) operated in the pulse-echo mode is utilized for insonification. Backscattered radio frequency (RF) data is collected and digitized at 500 megasamples per second utilizing a Tektronic DSA 601 digitizing oscilloscope (Beaverton, Oreg.) with 8-bit resolution. A variable gain system is used to increase the effective dynamic range of this digitizer. Radio frequency data are acquired from approximately 100 independent sites from each region of interest with 250 micron lateral step resolution.

A radio frequency peak-detected scan of the data is converted into a gray scale (0=lowest scattering, 255= highest scattering) map of the disc to allow visual inspection and selection of regions of interest for integrated backscatter analysis. Radio frequency ultrasonic data are stored in a raster scan format and analyzed with custom software. Segments of the RF lines are gated for integrated backscatter (IB) analysis to encompass the front and back surfaces of the nitrocellulose disc. The data are multiplied by a rectangular window and their power spectra are determined by fast-Fourier transformation. The power spectra from the specimens referenced to the power spectrum returned from a near-perfect steel planar reflector and the frequency-dependent backscatter transfer function across the useful bandwidth of the transducer (5 to 15 MHz) are computed and expressed in decibels relative to acoustic scattering from the near perfect steel plate reflector (Wong et al., Ultrasound in Med. & Biol. 1993; 19: 365–374). Integrated backscatter is computed as the average of the frequency-dependent backscatter transfer fimction across the useful bandwidth of the transducer.

Discs incubated with biotinylated perfluorocarbon emulsion have central regions with high acoustic scattering relative to the peripheral regions of the same disc and central regions of the control disc. Nitrocellulose discs incubated with the control emulsion have no central high scattering regions and no differences in acoustic character are detected between the central and peripheral regions of the disc. IB of the biotinylated emulsion coated nitrocellulose (−2.4±0.7 dB) was greater by 8.8±0.3 dB (approximately 8-fold ($p<0.05$)) than that from the control disc (−11.2±0.4 dB) over the 5 to 15 MHz frequency range. The frequency-dependent variation in apparent backscatter transfer function (mean±SEM) of the biotinylated and control emulsion discs are presented in FIG. 8. A smooth and consistently greater acoustic response is noted across the frequency spectrum due to the bound biotinylated emulsion. These data confirm and extend the findings of Examples 4, 5 and 6 with avidin and D-dimer, demonstrating that biotinylated perfluorocarbon emulsions with large particle sizes can be bound through a specific, targeting ligand system and significantly enhance the acoustic backscatter of a solid support surface. This improved acoustic backscatter is detected at clinically relevant ultrasonic frequencies, 5 to 15 MHZ.

EXAMPLE 8

Biotinylated perfluorocarbon emulsion is targeted to a plasma thrombi using biotinylated antifibrin monoclonal antibodies (NIBIHIO; Tymkewycz et al. 1993. Blood Coagulation and Fibrinolysis 4:211–221) and avidin. In a representative study (1 of 5), whole porcine blood is obtained and anticoagulated (9:1, v/v) with sterile sodium citrate. Blood is centrifuged at 1500 RPM at room temperature and the plasma fraction is obtained and stored at 4° C. Two porcine plasma thrombi are produced by combining plasma, 100 MM calcium chloride (3:1 v/v) and 2–5 U thrombin in a plastic tube through which 5-0 Vicryl suture is passed. Thrombi are allowed to coagulate at room temperature.

One thrombus is incubated with 150 ug antifibrin monoclonal antibody in 10 ml PBS with 1% bovine serum albumin (BSA) for two hours and a second control thrombus is incubated in PBS with 1% BSA. The antibody treated thrombus is then incubated with 0.5 mg avidin in 10 ml PBS with 1% BSA for 30 minutes. The control thrombus remains in PBS with 1% BSA. Both thrombi are washed extensively with PBS. Each thrombus is incubated with 300 $\mu l$/10 ml PBS of either biotinylated or control emulsion for 30 minutes. All thrombi are reexposed to emulsion twice to ensure uniform coverage and ultrasonically insonified (FIG. 9). Ultrasonic imaging is performed using a 7.5 MHz focused, linear phased array transducer and a Hewlett Packard Sonos 2500 Imaging System (Hewlett Packard, Inc., Andover, Mass.). All ultrasonic recordings are produced with fixed gain, compensation and time-gain compensation levels and are recorded on to SVHS videotape for subsequent image analysis. Average pixel grayscale over an extensive region of interest was sampled for 21 independent freeze-frame images for each thrombus using NIH Image 1.47 (National Institutes of Health; FIG. 10). The biotinylated perfluorocarbon emulsion is found to provide a marked acoustic enhancement of the surface. Average pixel grayscale levels of the biotinylated emulsion thrombus are 79.5±2.5 whereas the brightness of the control was markedly less (34.8±2.2, $p<0.05$). These results demonstrate the ability of biotinylated perfluorocarbon emulsion to target and acoustically enhance a biological tissue (i.e. thrombus) in vitro.

EXAMPLE 9

Biotinylated perfluorocarbon emulsion is targeted via biotinylated antifebrin antibodies (NIB5F3 and NIBIH10 Tynikewycz et al. 1993. Blood Coagulation and Fibrinolysis 4:211–221) to an isolated femoral artery thrombus in six mongrel dogs. A mongrel dog is anesthetized with sodium pentobarbital induction and halothane anesthesia. The right femoral artery and all branches are isolated at the level of the saphenous branch. A silver plated copper wire attached to a 22 ga. right angled needle point, insulated with plastic tubing (polyethylene P-240), is inserted into the femoral artery and secured with 4-0 Prolene suture. A current of 200–400 $\mu A$ is applied for up to two hours. Thrombus formation is monitored with continuous wave doppler and discontinued after an approximately 50% increase in circulation velocity is noted distal to the electrical injury. Adventitial discoloration secondary to the current is appreciated proximal to the entry point of the wire. A 20 ga. catheter is inserted into a proximal branch of the femoral artery and secured with 4-0 silk suture. A pressurized 0.9% NaCl drip is attached through a three-way stopcock to the catheter. Blood flow into the isolated segment is disrupted by proximal snare ligature. Excess blood is flushed from the arterial segment to inhibit further thrombus formation by infusion of saline for 15 minutes. The distal draining branches of the femoral artery are ligated or snared with suture. Biotinylated antifibrin monoclonal antibody (50 µg/1.0 ml PBS) is injected via the catheter and flushed with a few drops of saline. The antibody is allowed to incubate for one hour then the snare ligature distal to the wire insertion is released and excess antibody is flushed through with saline for five minutes. The distal femoral artery is reoccluded and avidin (250 µg/1.0 ml PBS) is infused and incubates for 30 minutes. The distal ligature is again released and excess avidin is flushed through with saline for five minutes. The distal ligature is reestablished and biotinylated perfluorocarbon emulsion is infused and incubates for 30 minutes. After the initial exposure of the thrombus to the emulsion, the unbound emulsion is washed through with saline. Thrombi are each exposed to avidin and biotinylated perfluorocarbon emulsion as described above. In three animals, the contra lateral artery is also isolated, partially occluded with electrically induced thrombi and exposed to a control perfluorocarbon emulsion analagous to the administration of biotinylated emulsion described above. Femoral arteries exposed to either control or biotinylated perfluorocarbon emulsion are ultrasonically imaged at 7.5 MHz with a focused, linear phased array transducer and a clinical Hewlett-Packard Sonos 2500 Ultrasonic Imaging System before and after contrast administration. Acutely formed thrombi, both control and contrast targeted, are not ultrasonically appreciated. For 6 of 6 femoral arteries, partially occlusive thrombi are markedly enhanced using the antifibrin targeted biotinylated perfluorocarbon contrast. In 3 of 3 femoral arteries thrombi, exposure to the control perfluorocarbon emulsion does not accentuate their acoustic reflectivity and these thrombi remain ultrasonically undetectable. FIG. 11 reveals a representative example of a femoral artery site of thrombus formation after electrical induction before and after exposure to antifibrin antibody and biotinylated contrast. In the pre-contrast image, the femoral artery is observed with a bright echogenic wire point anode protruding into the lumen but no thrombus is appreciated. After treatment with the biotinylated contrast emulsion, a large partially occluded thrombus is clearly noted by the enhanced acoustic reflectivity (FIG. 11). Again, no thrombus is appreciated in the control artery before or after exposure to control emulsion. These results demonstrate the concept of using bound perfluorocarbon emulsion to acoustically enhance biological surfaces, such as thrombotic tissue, in vivo to enable detection with a commercially available ultrasound imaging system.

EXAMPLE 10

Biotinylated perfluorocarbon emulsion, approximately 250 nm diameter, is targeted to prostatic carcinoma using monoclonal antibodies specific for prostate specific antigen (PSA) and are acoustically detected using polar, high frequency, high resolution acoustic microscopy. Representative examples of human prostatic carcinoma tissues are routinely processed by immersion fixation in 10% neutral buffered fon-nalin and embedded in paraffin. Twenty micron sections are prepared for acoustic microscopy; 5 micron sections are used for optical studies. All histologic sections are mounted on acid cleaned glass slides that have been coated with poly-L-lysine. All mounted sections are heated at 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Prostate sections are incubated with anti-PSA primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for 1 hour at room temperature. After rinsing in PBS, a 30 micron section is prepared for acoustic microscopy. A section for light microscopy (5 micron) is incubated with avidin biotin-peroxidase complex (VectaStain Elite Kit, Vector Lab) for 1 hour at room temperature. This section is rinsed in phosphate buffer (pH 7.6) and immersed in a solution of 3,3'-diaminobenzidine tetrahydrochloride (Sigma Chemicals, St. Louis, Mo.; 0.5 mg/ml in phosphate buffer, pH 7.6, containing 0.003% [v/v] hydrogen peroxide) for approximately ten minutes. The chromogenic precipitate is optically enhanced by brief immersion of stained sections in 0.125% (w/v) osmium tetroxide. The section is then rinsed in tap water, counterstained in Harris' hematoxylin, dehydrated in graded ethanols and Americlear, and mounted in a synthetic mounting medium.

After the second biotinylated antibody is incubated and washed, slides for acoustic microscopy are incubated in avidin (1.0 mg/–20cc PBS) using a bath on a rotating table for 30 min. Excess avidin is washed away with isotonic PBS buffer, pH 7.4–7.5 in three minute washes. Slides are incubated with biotinylated or control perfluorocarbon emulsion for twenty minutes (0.5 cc/–20.0 ml PBS), washed briefly with isotonic PBS 3× for 5 minutes each and reincubated with avidin (1.0 mg/–20cc) for 15 minutes. Excess avidin is rinsed off with three, 5 min. washes in PBS. The slide is then reincubated at above concentrations with biotinylated or control perfluorocarbon emulsion for 20 minutes. Unbound emulsion is washed away in three changes of PBS (5 minutes each) and the slides are transferred to the acoustic microscope for analysis.

The mounted specimens are each immersed into isotonic, phosphate buffered saline at room temperature for ultrasonic insonification. A custom designed acoustic microscope is used to collect ultrasonic data. The microscope consists of 50 MHz broadband, focused, piezoelectric delay-line transducer (¼ inch diameter, ½ inch focal length, 62 micron beam diameter, Model V390, Panametrics Co., Waltham, Mass.) operated in the pulse-echo mode. A Tektronix DSA 601 digitizing oscilloscope (Beaverton, Oreg.) is used to digitize 35 degree polar backscattered radio frequency (rf) data at 500 megasamples per second with 8-bit resolution. A variable gain system is used to increase the effective dynamic range of this digitizer. Radio frequency data is acquired from approximately 100 independent sites from each specimen with 50 micron lateral step resolution.

The rf data is stored in a low resolution raster scan fonnat and analyzed with custom software. Segments of the rf lines are gated for integrated backscatter analysis to encompass the front surface (i.e. excluding the back wall). The gated data are multiplied by a Hamming window and their power spectra are determined by fast-Fourier transformation. Power spectra within a tissue section are compared directly without reference to a steel plate. Integrated backscatter (IB)

is computed from the average of the frequency-dependent backscatter transfer function across the useful bandwidth of the transducer (30 to 55 MHz). Immunostained tissues are reviewed using a Nikon Optiphot-2 microscope for regions of PSA positive staining and the acoustic characteristics are compared. The net change in the apparent backscatter transfer function between the normal prostatic stroma and carcinomatous regions are clearly increased in sections treated with PSA targeted biotinylated versus the control perfluorocarbon emulsion across the frequency spectrum (30 to 55 MHz; FIG. 12). Biotinylated perfluorocarbon emulsion increases ($p<0.05$) the integrated backscatter from regions of prostatic cancer (47.17± dB) versus normal stromal (40.79±1.18 dB) by 6.38 dB (approximately 4-fold). In the control tissue sections, the integrated backscatter from the region of prostatic carcinoma (39.63±1.63 dB) was greater ($p<0.05$) than that from the normal stromal areas (36.13±2.17 dB) by approximately 3.5 dB (2-fold), reflecting inherent differences in acoustic character between normal and cancerous prostatic tissue. However, the targeted biotinylated perfluorocarbon emulsion amplified ($p<0.05$) these inherent differences by approximately 2-fold (2.87 dB; FIG. 13). These results clearly demonstrate the ability of site-targeted biotinylated perfluorocarbon emulsion to specifically enhance acoustic detection of prostate cancer in vitro.

EXAMPLE 11

Biotinylated perfluorocarbon emulsion, approximately 250 nm diameter, is targeted to ovarian carcinoma using monoclonal antibodies specific for OC-125 antigen and are acoustically detected using polar, high frequency, high resolution acoustic microscopy. Representative examples of human ovarian, carcinoma tissues are routinely processed by immersion fixation in 10% neutral buffered formalin and embedded in paraffin. Twenty micron sections are prepared for acoustic microscopy; 5 micron sections are used for optical studies. All histologic sections are mounted on acid cleaned glass slides that have been coated with poly-L-lysine. All mounted sections are heated to 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Ovarian sections are incubated with anti-OC-125 primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for 1 hour at room temperature. After rinsing in PBS, duplicate 30 micron sections are prepared for acoustic microscopy. Sections for light microscopy (5 micron) are incubated with avidin biotin-peroxidase complex (VectaStain Elite Kit, Vector Lab) for 1 hour at room temperature. Sections are rinsed in phosphate buffer (pH 7.6) and immersed in a solution at 3,3' diaminobenzidine tetrahydrochloride (Sigma Chemicals, St. Louis, Mo.; 0.5 mg/ml in phosphate buffer, pH 7.6, containing 0.0003% [v/v] hydrogen peroxide) for approximately ten minutes. The chromogenic precipitate is optically enhanced by brief immersion of stained sections in 0.125% (w/v) osmium tetroxide. Sections are then rinsed in tap water, counterstained in Harris' hematoxylin, dehydrated in graded ethanols and Americlear, and mounted in a synthetic mounting medium.

After the second biotinylated antibody is incubated and washed, slides are incubated in avidin (1.0 mg/–20 cc PBS) using a bath on a rotating table for 30 min. Excess avidin is washed away with isotonic PBS buffer, pH 7.4–7.5 in three 5 minute washes. The prepared slides are incubated with biotinylated or control perfluorocarbon emulsion for twenty minutes (0.5 cc/–20.0 ml PBS), washed briefly with isotonic PBS 3× for 5 minutes each and rewashed in avidin (1.0 mg/–20 cc) for 15 minutes. Excess avidin is rinsed off with three, 5 min. washes in PBS. Slides are then reincubated at above concentrations with biotinylated or control perfluorocarbon emulsion for 20 minutes. Unbound emulsion is washed away in three changes of PBS (5 minutes each) and the slides are transferred to the acoustic microscope for analysis.

The mounted specimens are each immersed into isotonic, phosphate buffered saline at room temperature for ultrasonic insonification. A custom designed acoustic microscope is used to collect ultrasonic data. The microscope consists of 50 MHz broadband, focused, piezoelectric delay-line transducer (¼ inch diameter, ½ inch focal length, 62 micron beam diameter, Model V390, Panametrics Co., Waltham, Mass.) operated in the pulse-echo mode. A Tektronix DSA 601 digitizing oscilloscope (Beaverton, Oreg.) is used to digitize 35 degree polar backscattered radio frequency (ro data at 500 megasamples per second with 8-bit resolution. A variable gain system is used to increase the effective dynamic range of this digitizer. Radio frequency data is acquired from approximately 100 independent sites from each specimen with 50 micron lateral step resolution.

The rf data are stored in a low resolution raster scan format and analyzed with custom software. Segments of the rf lines are gated for integrated backscatter analysis to encompass the front surface (i.e. excluding the back wall). The gated data are multiplied by a Hamming window and their power spectra are determined by fast-Fourier transformation. Integrated backscatter is computed from the average of the frequency-dependent backscatter transfer function across the useful bandwidth of the transducer (30 to 55 MHz). The power spectra from the specimens are referenced to the power spectrum returned from a glass microscope slide. IB is expressed in decibels relative to the scattering from the glass slide. Immunostained tissues are reviewed using a Nikon Optiphot-2 microscope for regions of PSA positive staining and the acoustic characteristics are compared.

The net change in the apparent backscatter transfer function between the normal ovarian stroma and carcinomatous regions are clearly increased in sections treated with OC-125 targeted biotinylated versus the control perfluorocarbon emulsion across the frequency spectrum (30 to 55 MHz; FIG. 14). Biotinylated perfluorocarbon emulsion increases ($p<0.05$) the integrated backscatter from regions of ovarian cancer (−28.19±1.39 dB) versus normal stromal (−38.75±0.84 dB) by 10.57 dB (greater than 8-fold). In the control tissue sections, the integrated backscatter from the region of ovarian carcinoma (−33.49±0.86 dB) was greater ($p<0.05$) than the normal stromal areas (−40.21±0.61 dB), approximately 6.72 dB (4-fold), reflecting inherent differences in acoustic character between normal and cancerous ovarian tissue. However, the targeted biotinylated perfluorocarbon emulsion amplified (p<0.05) these inherent differences by approximately 2-fold (3.84 dB; FIG. 15). These results clearly demonstrate the ability of site-targeted biotinylated perfluorocarbon emulsion to specifically enhance acoustic detection of ovarian cancer in vitro.

EXAMPLE 12

Biotinylated perfluorocarbon emulsion, approximately 250 nm diameter, is targeted to the epithelial capsule of tonsil using monoclonal antibodies specific for cytokeratin, CD-20, and BCL-2 antigens and are acoustically detected using polar, high frequency, high resolution acoustic microscopy. Representative examples of human tonsil are routinely processed by immersion fixation in 10% neutral buffered formalin and embedded in paraffin. Twenty micron sections are prepared for acoustic microscopy; a 5 micron section is used for optical studies. All histologic sections are mounted on acid cleaned glass slides that have been coated with poly-L-lysine. All mounted sections are heated at 55° C. for 1 hour in an oven.

Prior to immunostaining, all sections are dewaxed in three changes of Americlear, and dehydrated in successive changes of 95% and 100% ethanol. Endogenous peroxidase activity is blocked only in sections prepared for optical studies by immersion in absolute methanol containing 0.6% (v/v) hydrogen peroxide for 30 minutes. These and all sections for acoustic microscopy are then rehydrated through graded ethanols and distilled water and placed in isotonic PBS (pH 7.4). All sections are incubated with target specific monoclonal antibodies.

Tonsil sections are incubated with a mixture of anti-CD-20, BCL-2, and cytokeratin primary monoclonal antibodies per the recommendations of the vendor for 18 hours at 4° C. in moisture chambers. After primary incubation, sections are rinsed in isotonic PBS, then overlain with a polyclonal biotinyl-horse anti-mouse immunoglobin (VectaStain Elite Kits, Vector Laboratories, Burlingame, Calif.) for I hour at room temperature. After rinsing in PBS, duplicate 30 micron sections are prepared for acoustic microscopy. Sections for light microscopy (5 micron) are incubated with avidin-biotin-peroxidase complex (VectaStain Elite Kit, Vector Lab) for 1 hour at room temperature. Sections are rinsed in phosphate buffer (pH 7.6) and immersed in a solution of 3,3'-diaminobenzidine tetrahydrochloride (Sigma Chemicals, St. Louis, Mo.; 0.5 mg/ml in phosphate buffer, pH 7.6, containing 0.003% [v/v] hydrogen peroxide) for approximately ten minutes. The chromogenic precipitate are optically enhanced by brief immersion of stained sections in 0.125% (w/v) osmium tetroxide. Sections are then rinsed in tap water, counterstained in Harris' hematoxylin, dehydrated in graded ethanols and Americlear, and mounted in a synthetic mounting medium.

After the second biotinylated antibody is incubated and washed, one slide is incubated in avidin (1.0 mg/–20 cc PBS) using a bath on a rotating table for 30 min. Excess avidin is washed away with isotonic PBS buffer, pH 7.4–7.5 in three 5 minute washes. The prepared slide is incubated with biotinylated perfluorocarbon emulsion for twenty minutes (0.5 cc/–20.0 ml PBS), washed briefly with isotonic PBS 3× for 5 minutes each and rewashed in avidin (1.0 mg/–20 cc) for 15 minutes. Excess avidin is rinsed off with three, 5 minute washes in PBS. The slides are reincubated at above concentrations with biotinylated perfluorocarbon emulsion for 20 minutes. Unbound emulsion is washed away in three changes of PBS (5 minutes each) and the slide is transferred to the acoustic microscope for analysis.

The mounted specimen is immersed into isotonic, phosphate buffered saline at room temperature for ultrasonic insonification. A custom designed acoustic microscope is used to collect ultrasonic data. The microscope consists of a 50 MHz broadband, focused, piezoelectric delay-line transducer (¼ inch diameter, ½ inch focal length, 62 micron beam diameter, Model V390, Panarnetrics Co., Waltham, Mass.) operated in the pulse-echo mode. A Tektronix DSA 601 digitizing oscilloscope (Beaverton, Oreg.) is used to digitize 35 degree polar backscattered radio frequency (rf) data at 500 megasamples per second with 8 bit resolution. A variable gain system is used to increase the effective dynamic range of this digitizer. Radio frequency data are collected from the entire specimen and a peak detected image is created of the section and compared with the inimunostained tissue image.

Immunostained tissue is examined and imaged using a Nikon Optiphot-2 microscope with a Javlin Chromachip 11 camera attachment. Images are routed through a Panasonic digital mixer model WJ-AVE5 to Panasonic SVHS video recorders, models AG- 1960 or AG 1970 and displayed upon an Sony Trinitron monitor. Images are captured using NuVista software (Truevision, Inc., Indianapolis, Ind. 46256) executing on a Macintosh LCIII microcomputer.

FIG. 16 compares tonsil acoustically imaged as a radio frequency peak detected scan at 100 micron lateral step resolution (a) with an optically imaged section immunostained with horseradish peroxidase (b). The epithelial capsule targeted by a mixture of anti-cytokeratin antibodies is distinctly stained with horseradish peroxidase and homologous regions in the acoustic image are "brightened" by the targeted biotinylated acoustic contrast. In FIG. 17 the radio frequency peak detected acoustic image at 100 micron step resolution (a) is enhanced to 50 micron lateral step resolution. The targeted biotinylated perfluorocarbon contrast is clearly seen acoustically enhancing the epithelial rim of the tonsil, analogous to the optical immunostained image. This example clearly demonstrates the fidelity of biotinylated perfluorocarbon contrast targeting for enhanced acoustic contrast of tissues, such as lymph nodes.

EXAMPLE 13

A Method to Chemically Couple Antibody to Perfluorocarbon Emulsion Particle.

Preparation of emulsion: The perfluorocarbon nanoparticle contrast agent is produced by incorporating 1,2-dipalmitoyl-sn-glycero-3-phosphoethanolamine-N-4-(pmaleimidophenyl)butyramide (MPB-PE) into the outer lipid monolayer of the emulsion. The emulsion is comprised of perfluorodichlorooctane, safflower oil, a surfactant co-mixture and glycerin. The surfactant co-mixture includes lecithin, cholesterol and MPB-PE which is dissolved in chloroform. The chloroform-lipid mixture is evaporated under reduced pressure, dried in a 50° C. vacuum oven overnight and dispersed into water by sonication. The suspension is transferred into a blender cup with perfluorodichloroocatane, safflower oil and distilled, deionized water and emulsified for 30 to 60 seconds. The pre-emulsified mixture is transferred to a microemulsifier and continuously processed at 10,000 PSI for three minutes. The completed emulsion is vialed, blanketed with nitrogen and sealed with stopper crimp seal until use. A negative control emulsion is prepared identically, except a nonderivatized phosphatidylethanolamine is substituted into the surfactant co-mixture. Particle sizes are determined in triplicate at 30° C. with a laser light scatter submicron particle size analyzer.

Preparation and Isolation of Tissue Factor F(ab)' Fragments: F(ab)' fragments of a specific antibody are generated and isolated using an immunopure F(ab)' preparation kit (Pierce, Rockford, Ill.). Typically, IgG antibody is dialyzed into 20 mm phosphate/10 mm EDTA buffer (pH 7.0), concentrated to 20 mg/ml and digested by immobilized papain. Solubilized F9(ab)' are purified from Fc fragments and undigested IgG protein using a protein A column. F(ab)' fragments are purified from excess cysteine using a G25–15-column and deoxygenated phosphate buffer (pH 6.7). Fraction identity is confirmed by routine SDS-PAGE procedures.

Conjugation of Tissue Factor F(ab)' With MPB-PE Derivatized Emulsion: F(ab)' fractions are pooled and combined with the MPB-PE derivatized emulsion (0.01 to 5.0 mg F(ab)'/ml of emulsion, preferably I to 2 mg F(ab)'/ml of emulsion). The mixture is adjusted to pH 6.7, sealed under nitrogen and allowed to react overnight at ambient temperatures with gentle, continuous mixing. The mixture may be subsequently dialyzed with a 300,000 MWCO Spectra/Por DispoDialyzer (Laguna Hills, Calif.) against 10 mM phosphate buffer (PH 7.2) to remove unconjugated F(ab)' fragments. The final emulsion is vialed under nitrogen and stored at 4° C. until use.

EXAMPLE 14

In vitro Targeting of Fibrin-Rich Plasma Thrombi Using A Fibrin-Targeted, One-Step Acoustic Contrast System.

Whole blood was obtained fresh and anticoagulated (9:1, v/v) with sterile sodium citrate. In a series of trials, plasma clots (9) were produced by combining plasma and 100 mM calcium chloride (3:1, v/v) with 5 units of thrombin (Sigma Chemical Company, St. Louis, Mo.) in a plastic tube overlying nitrocellulose membranes. The plasma was allowed to coagulate slowly at room temperature.

Plasma clots were incubated with anti-fibrin (fab) conjugated or non-conjugated control emulsion contrast using antifibrin monoclonal antibodies (NIB-5F3 or NIB-1 H 10) (Tymkewycz et al. 1992; Tymkewycz et al. 1993). Half of the clots (5) were incubated individually with 150 g biotinylated antifibrin monoclonal antibody in 10 ml PBS with 1% bovine serum albumin, (crystallized, Sigma Chemical Company, St. Louis, Mo.) for two hours; the remaining clots (4) were maintained in PBS with 1% bovine serum albumin. Bovine serum albumin was added during antibody incubations to minimize nonspecific protein binding to the polystyrene petri dish walls. The anti-fibrin targeted emulsion was incubated with clots (0.2 ml) for 30 minutes. Control clots were treated similarly with a nontargeted control perfluorocarbon emulsion (0.2 ml) for 30 minutes. The plasma clots on nitrocellulose were insonified using an acoustic microscope to assess the change in ultrasonic backscattered power attributable to the control and targeted emulsions.

The microscope consisted of a 50 MHZ broadband, focused, piezoelectric delay-line transduce (¼ inch diameter, ½ inch focal length, Model V390, Panametrics Co., Waltham, NIA) operated in the pulse-echo mode. A Tektronix DSA 601 digitizing oscilloscope (Beaverton, Oreg.) was used to digitize backscattered radiofrequency data at 500 megasamples per second with 8-bit resolution. Radiofrequency data collected from each site was averaged 32 times. Averaged radiofrequency data were acquired from approximately 400 independent sites with 50 micron lateral step resolution. The radiofrequency data are stored in a low resolution raster scan format and analyzed with custom software. Segments of the radiofrequency lines, 500 nsec in duration and encompassing surface reflection are gated for analysis. The gated data are multiplied by a Hamming window and their power spectra determined by fast-Fourier transformation.

The power spectra from each specimen was referenced to the power spectrum backscattered from a near-perfect steel plate reflector to compute the apparent frequency dependent backscatter transfer function. The backscatter transfer function for the acoustic reflectivity of the smooth cells, B(t), was expressed in decibels relative to the power reflected from the steel plate:

$$B(f)^2 = 10 \log[V_{(f)}^2{}_{tissue}]/[V_{(f)}^2{}_{steel\ plate}]$$

where $V_{(f)}^2{}_{tissue}$ is the power at selected frequency of the gated rf backscattered from the cells and $V_{(f)}^2{}_{steel\ plate}$ is the power at the same frequency of the gated rf backscattered from the steel plate. Integrated backscatter (IB) was computed from the average of the frequency-dependent backscatter transfer function over the useful bandwidth of the transducer (FIG. 18).

EXAMPLE 15

Scanning Electron Micrographs Identification of Tissue Factor Epitopes On Surfaces of Cultured Endothelial Cells Using the One-Step, Tissue Factor Targeted Nanoparticle Emulsion.

Porcine aorta smooth muscle cells known to express tissue factor in abundance on their cell surface were cultured onto 12 mm round, glass cover slips and grown for 48 hours at 37° C. under 5% $CO_2$. Four treatment groups were prepared: 1) cells alone (untreated control); 2) cells exposed to a nontargeted control emulsion (negative control); 3) cells exposed to anti-tissue factor antibody before treatment with tissue-factor targeted emulsion (blocked control); and 4) cells treated with tissue-factor targeted emulsion. All smooth muscle cell cultures were fixed in 2.5% glutaraldehyde in PBS for one hour, rinsed briefly in PBS and post-fixed in 2% osmium tetroxide for 1 hour. The fixed and washed cells were dehydrated in ascending concentrations of ethyl alcohol, 10 minutes/step: 50%, 70%, 90% and 3×100% followed by three 15-minute washes in hexatnethyldisilazane (Electron Microscopy Sciences, Forth Worth, Pa.). The glass slips supporting the fixed cells were placed on stubs and imaged with a scanning electron microscope.

Figure 19:
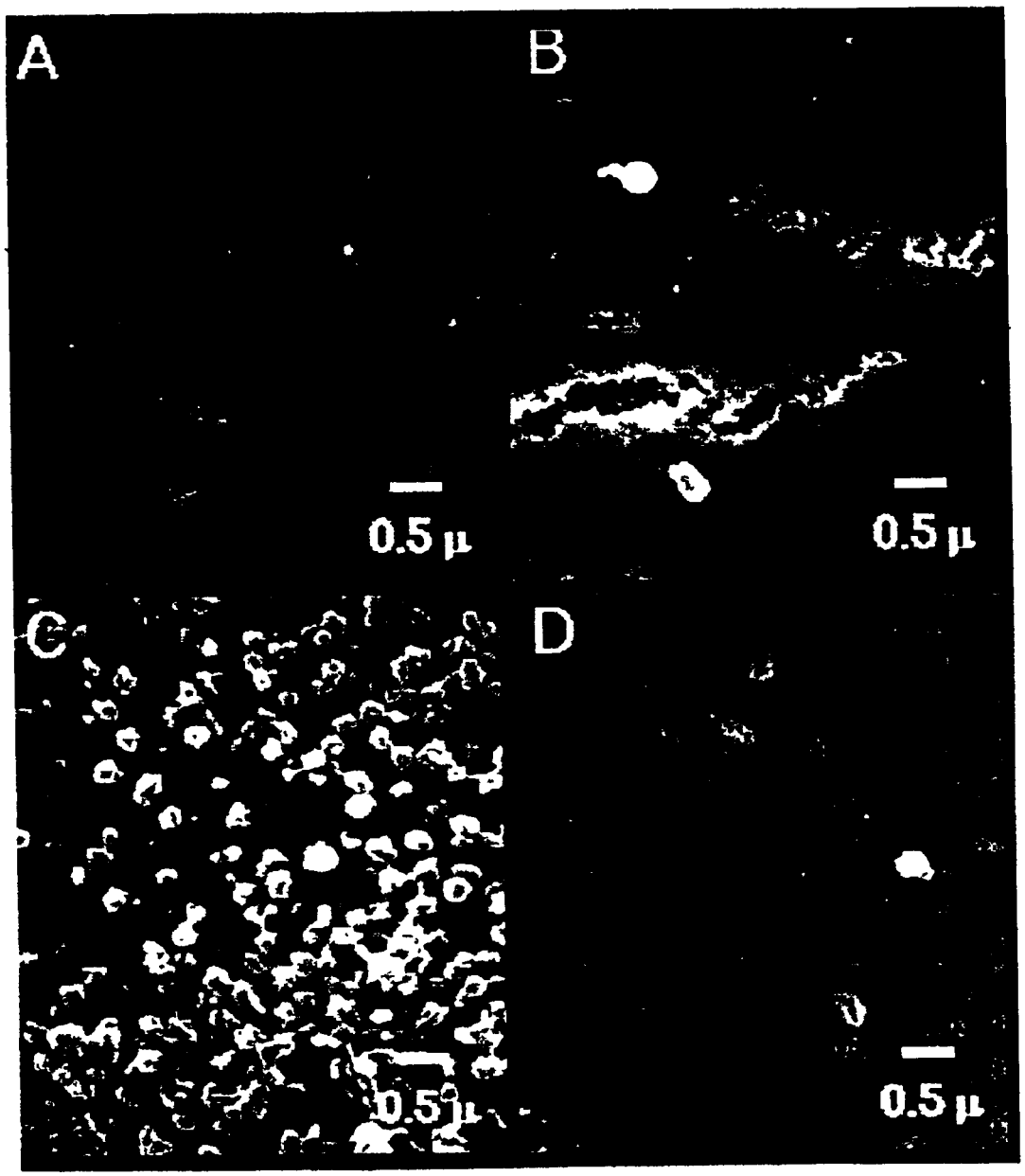

Only trace nonspecific binding was appreciated in cell cultures treated with no (FIG. 19A) or untargeted control emulsion (FIG. 19B). Tissue factor targeted specifically bound to the aortic smooth muscle cells (FIG. 19C) and this binding could be specifically blocked by anti-tissue factor antiserum (FIG. 19D). These results demonstrate the ligand specificity of the targeted perfluorocarbon nonospheres.

EXAMPLE 16

Figure 20:
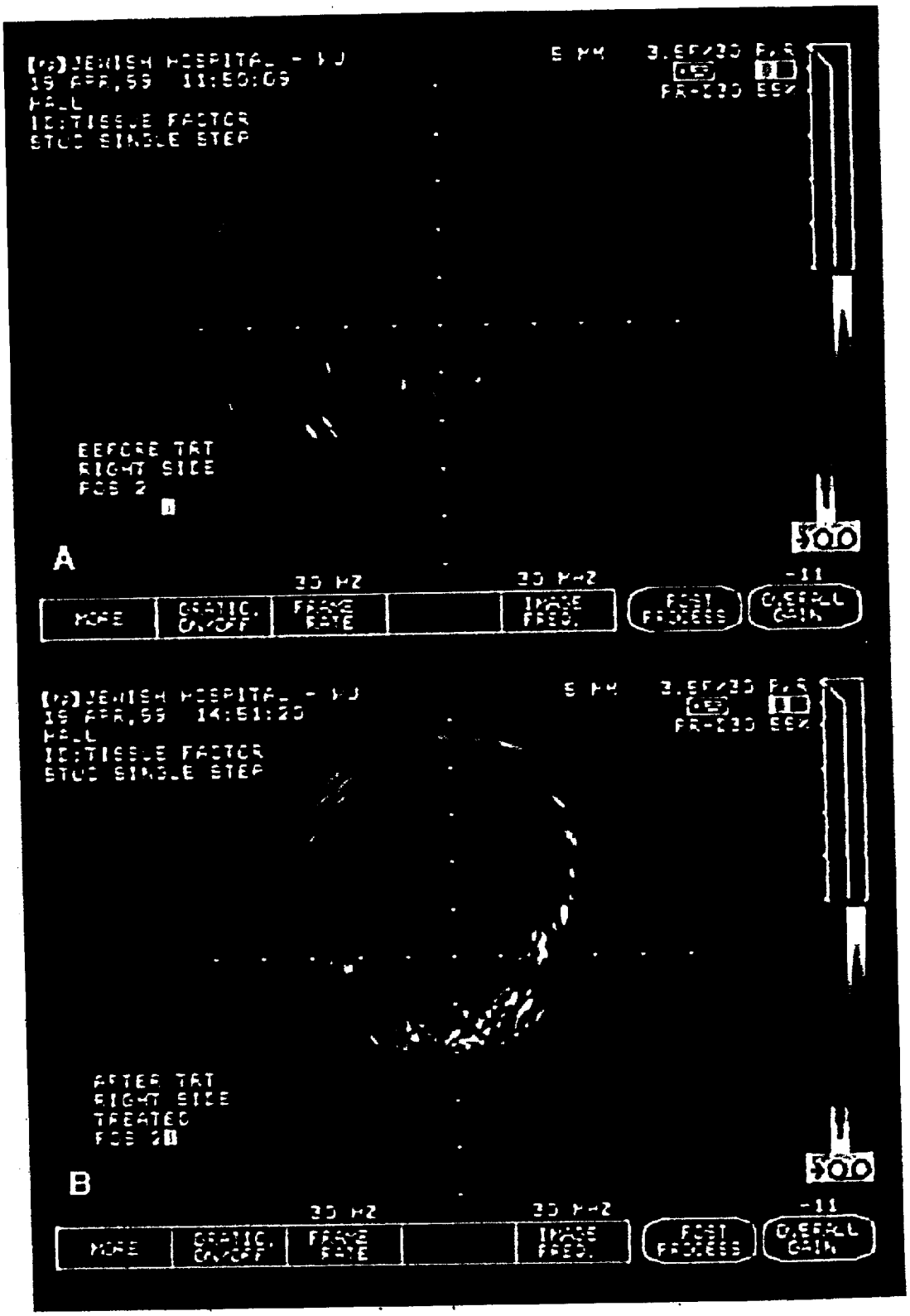

Local Delivery of One-Step Tissue Factor Targeted Nanoparticle Emulsion In Balloon-Injured Arteries In Pigs:

Briefly, pigs weighing approximately 20 kg were anesthetized with telazol cocktail (1 ml/23 kg IM) followed by 1–2% isoflurane in oxygen. Both common carotids were exposed aseptically; and the distal portion of each, proximal to the bifurcation of the internal carotid artery, was cannulated and connected to a Touhy adapter. The right femoral artery was exposed, and an 8 French sheath was inserted through which a guide catheter and 8 mm balloon catheter was directed to each carotid using an exchange wire. The balloon was inflated five times with sequentially increased pressure up to 6 atmospheres for 30 seconds with one minute between inflations. Prior to the fifth balloon deflation, heparinized (10 units/ml) saline was infused through the distal Touhy access. As the catheter was slowly deflated for the final time and withdrawn from the common carotid, the residual blood within was flushed from the artery. When the catheter was free of the carotid artery, a proximal snare was placed, isolating the carotid segment containing buffer. The anti-tissue factor targeted nanoparticulate emulsion (0.5 ml) was infused into the right carotid artery and allowed to incubate for 2 hours. After 2 hours the formulation was removed, and the artery was washed with 0.9% NaCl. The left carotid artery was exposed to an nonspecific f(ab) conjugated nanoparticulate emulsion. Vessels were ultrasonically imaged on each side following the formulation washout (FIG. 20).

Following angioplasty, but prior to application of contrast agent, carotid arterial walls exhibited no evidence of augmented acoustic reflectivity secondary to overstretch injury alone. Exposure to the control nonspecific emulsion did not alter the acoustic character of the arterial wall. However, the tissue factor targeted emulsion agent clearly penetrated the vascular tissue and localized to the media where increased tissue factor expression was inducted, resulting in substantial augmentation of acoustic contrast. Acoustic enhancement was not circumferentially distributed, but was concentrated over one-half to two-thirds of the vessel wall where non-circumferential force was applied by the angioplasty balloon.

Immunohistochemistry: Vessel segments were fixed in molecular biology fixative (Streck Laboratories, Omaha, Nebr.), embedded in paraffin, cut at 5,uM, and mounted on gelatin-coated slides. A slide from each vessel was stained with Verhoeff s van Gieson elastin stain to verify rupture of the internal elastic lamina as an index of deep vascular injury. For immunohistochemistry, the tissue sections were deparaffinized with xylene, hydrated with a descending ethanol series, and rinsed with PBS. Endogenous peroxidase activity was blocked by incubation for 30 minutes with hydrogen peroxide in methanol. Nonspecific binding of antibody was blocked by incubation for 45 minutes in PBS containing 1% bovine serum albumin, 0.3% triton X-100, 10% normal goat serum, and 1% normal pig serum. The sections were incubated overnight at 4° C. with the rabbit anti-pig tissue factor antibody diluted 1:100 in the blocking solution. After rinsing the slides with PBS, the sections were incubated for 45 minutes at room temperature with biotinylated goat anti-rabbit IgG (Vector Laboratories) diluted 1:200 with blocking buffer. The sections were stained with AEC (HistostainPlus, Zymed) and counterstained with hematoxylin.

Immunohistochemistry revealed a pattern of localization of tissue factor in balloon-injured vessels in the media (arrows) at the site of acoustic contrast enhancement, as well as on the intimal surface associated with inflammatory cells (FIG. 21A; L=Iumen). In contrast, control uninjured vessels exhibited staining primarily in the adventitia and not in the tunica media (FIG. 21B). No obvious dissections of the arterial walls were observed microscopically, although some mild fenestration of the internal elastic lamina was noted. These results demonstrate the presence of tissue factor only in the media of balloon overstretched arteries. The vessels were acoustically enhanced by the tissue factor targeted, one-step nanoparticulate emulsion, but not by the nontargeted control nanoparticulate emulsion.

In view of the above, it will be seen that the several objects of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for enhanced magnetic resonance imaging of a target tissue in a subject in vivo which method comprises
   detecting a magnetic resonance image of said target tissue wherein said target tissue is bound to a ligand specific for said target tissue and wherein said ligand is directly coupled to lipid-coated particles consisting of liquid perfluorocarbon, said coated particles contained in an emulsion,
   which method further comprises, prior to said detecting, administering said emulsion to said subject.

2. The method of claim 1, wherein said lipid-coated particles further comprise at least one chemotherapeutic agent or gene therapy delivery system.

3. The method claim 1, wherein said ligand comprises an antibody or fragment thereof, a virus, a receptor agonist or antagonist, a hormone, or a nucleic acid.

4. The method of claim 3, wherein the ligand is an antibody or fragment thereof.

5. A method for enhanced magnetic resonance imaging of a target tissue in a subject in vivo which method comprises administering to said subject an emulsion comprising a ligand specific for said target tissue, said ligand directly coupled to lipid-coated particles consisting of liquid perfluorocarbon, and
   detecting a magnetic resonance image of said target tissue wherein said target tissue is bound to said ligand and wherein said ligand is directly coupled to lipid-coated particles contained in said emulsion.

6. The method of claim 5, wherein said lipid-coated particles further comprise at least one chemotherapeutic agent or gene therapy delivery system.

7. The method of claim 5, wherein said ligand comprises an antibody or fragment thereof, a virus, a receptor agonist or antagonist, a hormone, or a nucleic acid.

8. The method of claim 7, wherein the ligand is an antibody or fragment thereof.

9. A method for magnetic resonance imaging of a target tissue in a subject in vivo which method comprises
   detecting a magnetic resonance image of said target tissue wherein said target tissue is bound to a ligand specific for said target tissue and wherein said ligand is directly coupled to lipid-coated particles consisting of liquid perfluorocarbon, said coated particles contained in an emulsion,
   wherein said subject has been administered said emulsion prior to said detecting.

10. The method of claim 9, wherein said lipid-coated particles further comprise at least one chemotherapeutic agent or gene therapy delivery system.

11. The method of claim 9, wherein said ligand comprises an antibody or fragment thereof, a virus, a receptor agonist or antagonist, a hormone, or a nucleic acid.

12. The method of claim 11, wherein the ligand is an antibody or fragment thereof.

* * * * *